(12) United States Patent
Patel et al.

(10) Patent No.: US 7,903,704 B2
(45) Date of Patent: Mar. 8, 2011

(54) TUNABLE QUANTUM CASCADE LASERS AND PHOTOACOUSTIC DETECTION OF TRACE GASES, TNT, TATP AND PRECURSORS ACETONE AND HYDROGEN PEROXIDE

(75) Inventors: C. Kumar N. Patel, Los Angeles, CA (US); Ilya Dunayevskiy, Los Angeles, CA (US); Manu Prasanna, Marina del Rey, CA (US); Rowel C. Go, Carson, CA (US); Alexei Tsekoun, Los Angeles, CA (US); Michael Pushkarsky, San Diego, CA (US); Richard Maulini, Los Angeles, CA (US)

(73) Assignee: Pranalytica, Inc., Santa Monica, CA (US)

( * ) Notice: Subject to any disclaimer, the term of this patent is extended or adjusted under 35 U.S.C. 154(b) by 401 days.

(21) Appl. No.: 11/821,528

(22) Filed: Jun. 22, 2007

(65) Prior Publication Data

US 2008/0159341 A1 Jul. 3, 2008

Related U.S. Application Data

(60) Provisional application No. 60/816,245, filed on Jun. 23, 2006, provisional application No. 60/873,649, filed on Dec. 8, 2006.

(51) Int. Cl.
*H01S 3/13* (2006.01)
(52) U.S. Cl. .................. 372/29.021; 372/29.014; 372/97
(58) Field of Classification Search ............. 372/29.014, 372/29.021, 97
See application file for complete search history.

(56) References Cited

U.S. PATENT DOCUMENTS

| 3,394,253 A | 7/1968 | Harrick et al. ................ 250/353 |
| 4,267,732 A | 5/1981 | Quate ............................ 73/606 |
| 4,516,858 A | 5/1985 | Gelbwachs ................... 356/437 |
| 4,795,253 A | 1/1989 | Sandridge et al. ............. 356/51 |

(Continued)

FOREIGN PATENT DOCUMENTS

FR 2595013 8/1987

(Continued)

OTHER PUBLICATIONS

Wysocki et al., "Widely tunable mode-hop free external cavity quantum cascade laser for high resolution spectroscopic applications", 2005, Appl. Phys. B 81, 769-777.*

(Continued)

*Primary Examiner* — Minsun Harvey
*Assistant Examiner* — Joshua King
(74) *Attorney, Agent, or Firm* — Cislo & Thomas, LLP

(57) ABSTRACT

Methods and apparatus for broad tuning of single wavelength quantum cascade lasers and the use of light output from such lasers for highly sensitive detection of trace gases such as nitrogen dioxide, acetylene, and vapors of explosives such as trinitrotoluene (TNT) and triacetone triperoxide (TATP) and TATP's precursors including acetone and hydrogen peroxide. These methods and apparatus are also suitable for high sensitivity, high selectivity detection of other chemical compounds including chemical warfare agents and toxic industrial chemicals. A quantum cascade laser (QCL) system that better achieves single mode, continuous, mode-hop free tuning for use in L-PAS (laser photoacoustic spectroscopy) by independently coordinating gain chip current, diffraction grating angle and external cavity length is described. An all mechanical method that achieves similar performance is also described. Additionally, methods for improving the sensor performance by critical selection of wavelengths are presented.

2 Claims, 31 Drawing Sheets

U.S. PATENT DOCUMENTS

| | | | | |
|---|---|---|---|---|
| 5,241,177 | A | 8/1993 | Albrecht | 250/338 |
| 5,347,527 | A | 9/1994 | Favre et al. | 372/20 |
| 5,528,040 | A | 6/1996 | Lehmann | 250/343 |
| 6,160,255 | A | 12/2000 | Sausa | 250/227 |
| 6,202,470 | B1 | 3/2001 | Chou | 73/24 |
| 6,366,592 | B1 * | 4/2002 | Flanders | 372/18 |
| 6,527,398 | B1 | 3/2003 | Fetzer | 356/437 |
| 6,594,289 | B2 * | 7/2003 | Yamada et al. | 372/20 |
| 6,614,828 | B1 | 9/2003 | Basting et al. | 372/100 |
| 6,683,895 | B2 | 1/2004 | Pilgrim et al. | 372/20 |
| 6,690,690 | B2 | 2/2004 | Marron | 372/20 |
| 6,807,217 | B2 | 10/2004 | Mueller | 372/102 |
| 6,847,661 | B2 | 1/2005 | Jerman et al. | 372/20 |
| 6,856,632 | B1 | 2/2005 | Heanue et al. | 372/20 |
| 6,862,301 | B2 | 3/2005 | Cox | 372/20 |
| 6,901,088 | B2 | 5/2005 | Li et al. | 372/20 |
| 6,912,235 | B2 | 6/2005 | Anthon et al. | 372/29 |
| 6,975,402 | B2 | 12/2005 | Bisson et al. | 356/432 |
| 7,004,909 | B1 | 2/2006 | Patel et al. | 600/532 |
| 7,012,696 | B2 | 3/2006 | Orr et al. | 356/454 |
| 2004/0179200 | A1 | 9/2004 | Yoon et al. | 356/432 |
| 2004/0211900 | A1 | 10/2004 | Johnson | 250/338 |
| 2005/0117157 | A1 | 6/2005 | Tarsa | 356/437 |
| 2005/0129073 | A1 | 6/2005 | Nguyen et al. | 372/20 |
| 2005/0207943 | A1 | 9/2005 | Puzey | 422/82 |
| 2006/0043301 | A1 | 3/2006 | Mantele et al. | 250/339 |

FOREIGN PATENT DOCUMENTS

| | | |
|---|---|---|
| WO | WO 2004/104562 | 12/2004 |
| WO | WO 2005/088275 | 9/2005 |
| WO | WO 2005/093390 | 10/2005 |
| WO | WO 2006/008557 | 1/2006 |

OTHER PUBLICATIONS

J. Faist, F. Capasso, DL Sivco, C. Sirtori, AL Hutchinson, and AY Cho, "Quantum Cascade Laser," Science, vol. 264, , pp. 553-556, 1994.

"Optical detection of chemical warfare agents and toxic industrial chemicals: Simulation", Michael E. Webber, Michael Pushkarsky, C. Kumar N. Patel, Journal of Applied Physics 97, 113101 (2005).

Jérome Faist, Claire Gmachl, Federico Capasso, Carlo Sirtori, Deborah L. Sivco, James N. Baillargeon, and Alfred Y. Cho "Distributed feedback quantum cascade lasers", Appl. Phys. Lett. 70, 2670 (1997).

G. P. Luo, C. Peng, H. Q. Le, S. S. Pei, W.-Y. Hwang, B. Ishaug, J. Um, J. N. Baillargeon, and C.-H. Lin, Appl. Phys. Lett. 78, 2834 (2001).

G. Luo, C. Peng, H. Q. Le, S.-S. Pei, H. Lee, W.-Y. Hwang, B. Ishaug, and J. Zheng, IEEE J. Quantum Electron. 38, 486 (2002).

"Systems for Tunable External Cavity Diode Lasers", Chapter 5 in Cunyun Ye, "Tunable External Cavity Diode Lasers", World Scientific, 2004.

G. Gentry, A. Grohn, H. Talvitie, M. Kaivola, and H. Ludvigsen, IEEE Journal of Quantum Electronics, vol. 36, No. 10, (2000).

I. P. Kaminow, G. Eisenstein and L. W. Stulz, "Measurement of the Modal Reflectivity of an Antireflection Coating on a Superluminescent Diode", IEEE Journal of Quantum Electronics, vol. QE-19, No. 4, Apr. 1983.

Michael Pushkarsky, Illya G. Dunayevskiy, Alexei G. Tsekoun, Rowell Go and C. Kumar N. Patel, "High-sensitivity detection of TNT", Proceedings of the National Academy of Sciences 103, 19630-19634 (2006).

A. Tsekoun, R. Go, M. B. Pushkarsky, M. Razeghi and C. K. N. Patel, Proc. Nat, Acad. Sciences 103, 4831-4835 (2006).

Michael Pushkarsky, Alexei Tsekoun, Ilya G. Dunayevskiy, Rowel Go, and C. Kumar N. Patel, "Sub-parts-per-billion level detection of NO2 using room-temperature quantum cascade lasers", Proceedings of the National Academy of Sciences 103, 10846-10849 (2006).

R. Wolfenstein, Chem Ber., 28, 2265-2269 (1895).

J. C. Oxley, J. L. Smith, K. Shinde and J. Moran, Propellants, Explosives, Pyrotechnics 30, 127-130 (2005) and references cited therein.

Ismael Cotte-Rodriguez, Hao Chen and R. Graham Cooks, Chem. Comms. 10, 953-955 (2006).

L. S. Rothman, A. Barbe, D. C. Benner, L. R. Brown, C. Camy-Peyret, M. R. Carleer, K. Chance, C. Clerbaux, V. Dana, V. M. Devi, A. Fayt, J.-M. Flaud, R. R. Gamache, A. Goldman, D. Jacquemart, K.W. Jucks, W.J. Lafferty, J.-Y. Mandin, S. T. Massie, V. Nemtchinov, D. A. Newnham, A. Perrin, C. P. Rinsland, J. Schroeder, K. M. Smith, M. A. H. Smith, K. Tang, R. A. Toth, J. Vander Auwera, P. Varanasi, and K. Yoshino, "The HITRAN Molecular Spectroscopic Database: Edition of 2000 Including Updates of 2001" Journal of Quantitative Spectroscopy & Radiative Transfer 82, p. 5-44, 2003.

Spacecraft Maximum Allowable Concentrations for Selected Airborne Contaminants: vol. 4 (National Academy of Sciences Press, 2000).

J. S. Yu, A. Evans, S. Slivken, S. R. Darvish, and M. Razeghi, Appl. Phys. Lett. 88, 251118 (2006).

S. R. Darvish, S. Slivken, A. Evans, J. S. Yu, and M. Razeghi, Appl. Phys. Lett. 88, 201114 (2006).

P. McNicholl and H. J. Metcalf, Appl. Opt. 24, 2757 (1985).

A. T. Schremer and C. L. Tang, IEEE Photon. Technol. Lett., 2, 3 (1990).

W. R. Trutna, Jr., and L. F. Stokes, J. Lightwave Technol., 11, 1279 (1993).

M. de Labachelerie and G. Passedat, Appl. Opt. 32, 269 (1993). See also: H. Lotem, Appl. Opt.33, 3816 (1994).

Lotem, H., Technical Note, Applied Optics V.33, No. 18, Jun. 1994, Mode-hop suppression of Litrow grating-tuned lasers: comment.

Favre, F. et al., Electronics Letters, V. 27, No. 2, Jan. 1991, 82 nm of Continuous Tunability for an Exerrnal Cavity Semiconductor Laser.

Favre, F. et al., Electronics Letters, V. 22, No. 15, Jul. 1986, External-Cavity Semiconductor Laser with 15 nm Continuous Tuning Range.

* cited by examiner

TUNABLE QUANTUM CASCADE LASERS AND PHOTOACOUSTIC DETECTION OF TRACE GASES, TNT, TATP AND PRECURSORS ACETONE AND HYDROGEN PEROXIDE

CROSS-REFERENCES TO RELATED APPLICATIONS

Applicant(s) and/or Inventor(s) hereby rescind any disclaimer and/or any arguments made in any prior related application. Such disclaimer(s) and/or argument(s) as well as any prior art relevant to such disclaimer(s) and/or argument(s) may need to be revisited by the Examiner.

This patent application is related to and claims priority from U.S. Provisional Patent Application Ser. No. 60/816,245 filed Jun. 23, 2006 for Sub-ppb Level Detection of $NO_2$ using Room Temperature Quantum Cascade Lasers as well as U.S. Provisional Patent Application Ser. No. 60/873,649 filed Dec. 8, 2006 for High Sensitivity Detection of TNT, which applications are incorporated herein by this reference thereto.

STATEMENT AS TO RIGHTS TO INVENTIONS MADE UNDER FEDERALLY-SPONSORED RESEARCH AND DEVELOPMENT

The technology disclosed herein was supported at least in part by NIST/ATP Grant 70NANB3H3026 and DARPA (Defense Advance Research Projects Agency) Contract HR0011-04-C-0102 (Approved for Public Release, Distribution Unlimited).

COPYRIGHT AUTHORIZATION

Portions of the disclosure of this patent document may contain material which is subject to copyright and/or mask work protection. The copyright and/or mask work owner has no objection to the facsimile reproduction by anyone of the patent document or the patent disclosure, as it appears in the Patent and Trademark Office patent file or records, but otherwise reserves all copyright and/or mask work rights whatsoever. 37 C.F.R. §1.71(d).

BACKGROUND OF THE INVENTION

1. Field of the Invention

This invention is directed to highly sensitive or ultrasensitive equipment and methods that detect trace amounts of gases by refined optical illumination and response detection as well as photoacoustic methods.

2. Description of the Related Art

Mid and long wave infrared quantum cascade lasers (QCLs) cover a very important spectral region from about 3 µm to 15 µm where most of the important trace gas pollutants, chemical warfare agents, toxic industrial chemicals, and vapors of explosives exhibit their characteristic infrared fingerprint absorption. Use of these QCLs for sensitive spectral analysis of the target gases requires a broad tunability of essentially single wavelength radiation and techniques for detection of the target gases at very low concentrations in the presence of normally occurring interferent gases whose infrared absorption fingerprints overlap with those of the targets.

Quantum cascade lasers as fabricated operate as Fabry-Perot cavity lasers formed by the end facets of the semiconductor laser chips and produce a multiwavelength output covering some hundreds of nanometers. The spectral position of each of the independently lasing wavelengths is determined by the Fabry-Perot cavity modes of the laser chip and the wavelength spread is determined by the gain width of the laser. Such broad spectral output is virtually useless for the highly sensitive and selective detection of the target gases. The laser output needs to be essentially one single wavelength and mechanisms are needed for broad tunability so that the fingerprint characteristic of the target gas absorption can be accurately measured. The broad tuning necessary for the sensitive and selective target gas detection has led to both software and hardware innovations.

Further, use of broadly tunable single wavelength radiation for sensitive detection of the target gases in a sample is complicated by the presence of other constituents, often called interferents, in the sample. The overlapping spectra signatures of the interferents and the target gases, obtained using broadly tunable single frequency lasers can be deconvolved using algorithms and techniques described in an earlier patent application, U.S. patent application Ser. No. 11/256,377 filed Oct. 21, 2005 for System and Method for High Sensitivity Optical Detection of Gases which shares co-inventors with this instant patent document and which is incorporated herein by this reference thereto.

SUMMARY OF THE INVENTION

In view of the foregoing disadvantages inherent in the known types of gas detectors now present in the prior art, the present invention provides a new and more sensitive gas detection system wherein the presence of selected gases can be readily determined at very low levels with a high degree of rejection of false signals arising from interferents.

The general purpose of the present invention, which will be described subsequently in greater detail, is to provide reliable and highly sensitive gas detection systems which are not anticipated, rendered obvious, suggested, taught, or even implied by any of the prior art gas detection systems, either alone or in any combination thereof.

In one embodiment of the present invention, a method for leveling the output of a multiwavelength laser system over a number of lasing wavelengths in a tuning window is set forth with the steps including the providing a laser gain chip and determining a first current change value needed to shift the laser gain chip's FP mode comb exactly one free spectral range. The laser system is then tuned with monitoring occurring for a second current change value from the initial point during the tuning. Remapping then occurs with the remapping of the second current change to the first current change when the second current change exceeds the first current change. Remapping takes place by subtracting the second current change from first current change such that laser output power varies minimally with laser wavelength as the second current change value for a tuned wavelength of the multiwavelength laser system is remapped onto the first current change value.

In another embodiment, a laser illumination system for providing laser light over a multiwavelength spectrum includes a multiwavelength laser light source emitting light and a wavelength-selective reflector in optical communication with the source. A translator coupled to the reflector displaces the reflector according to a first signal and controls a distance between the reflector and the source. A rotation stage is coupled to the translator. The rotation stage rotates the reflector according to a second signal and controls an angle between the reflector and the source such that single mode, continuous, mode-hop free tuning is provided by the laser illumination system.

In a third embodiment, a method for more quickly determining the presence of a target gas includes the steps of identifying and selecting regions in a frequency range of a selectable wavelength light source which meets all the following criteria: the target gas has large absorption in at least some frequencies in the frequency range, expected interferents have low absorption at their expected concentrations, and a detectable signature of the target gas is linearly independent of signature of interferents. A sample of gas is collected for testing of the target gas and a scan is performed across the identified and selected regions with the collecting of photoacoustic data from the scan. The photoacoustic data is linearly deconvolved against a standardized library of the target gas and list of expected interferents to obtain a gas concentration measurement for the target gas.

At least three key innovations are provided the technology disclosed herein.

The first is a software-implemented algorithm (or method) that provides tuning capability of the single wavelength QCL output such that under computer control, the laser wavelength can be reproducibly tuned over a very broad spectral region without experiencing any mode hops or jumps. The computer simultaneously controls the QCL drive current, the angle of the wavelength selective grating and the over-all cavity length. Furthermore, an all-mechanical system is provided that automatically and in a highly-coordinated fashion provides the cavity length adjustment as the angle of the grating is changed. When performed in tandem, these coordinated actions enable selection of the desired operating wavelength of the QCL.

Second, a laser wavelength tuning algorithm/method is achieved by creating a "Smart Grid" of interrogating wavelengths that simultaneously focus on the unique features of the fingerprint absorption of the desired targets while eliminating those wavelengths at which the key interferents may have their sharp absorption features. Use of appropriate Smart Grids improves the ROC (receiver operational characteristic) curves, i.e., the characteristic describing the detection threshold versus probability of false alarms (PFA) and reduces the time it takes to make a measurement.

Third, performance optimization of the tunable QCL based trace gas detection scheme is achieved by iteratively changing the measurement algorithms in a learning mode as the instrumentation carries out the trace gas detection.

Additionally, for speeding up the process of data collection without jeopardizing the selectivity desired in the target gas detection, described by receiver operational characteristic (ROC) curves, we describe schemes that avoid measurement of the sample gas absorptions at wavelengths that correspond to strong but sharply defined absorptions of the interferent gases. One such scheme is called the Smart Grid algorithm and has proven to be very successful in the detection of traditional and homemade explosives and their precursors.

Other embodiments of the present invention are set forth in more detail, below, and the embodiments set forth above are made for purposes of example only and not of limitation.

BRIEF DESCRIPTION OF THE DRAWINGS

FIG. 22 shows a schematic cross section of a configuration for mode-hop-free tuning system. The point B moves along the optical axis b and the point A moves along a perpendicular axis a.

DESCRIPTION OF THE PREFERRED EMBODIMENT(S)

Figure 1:
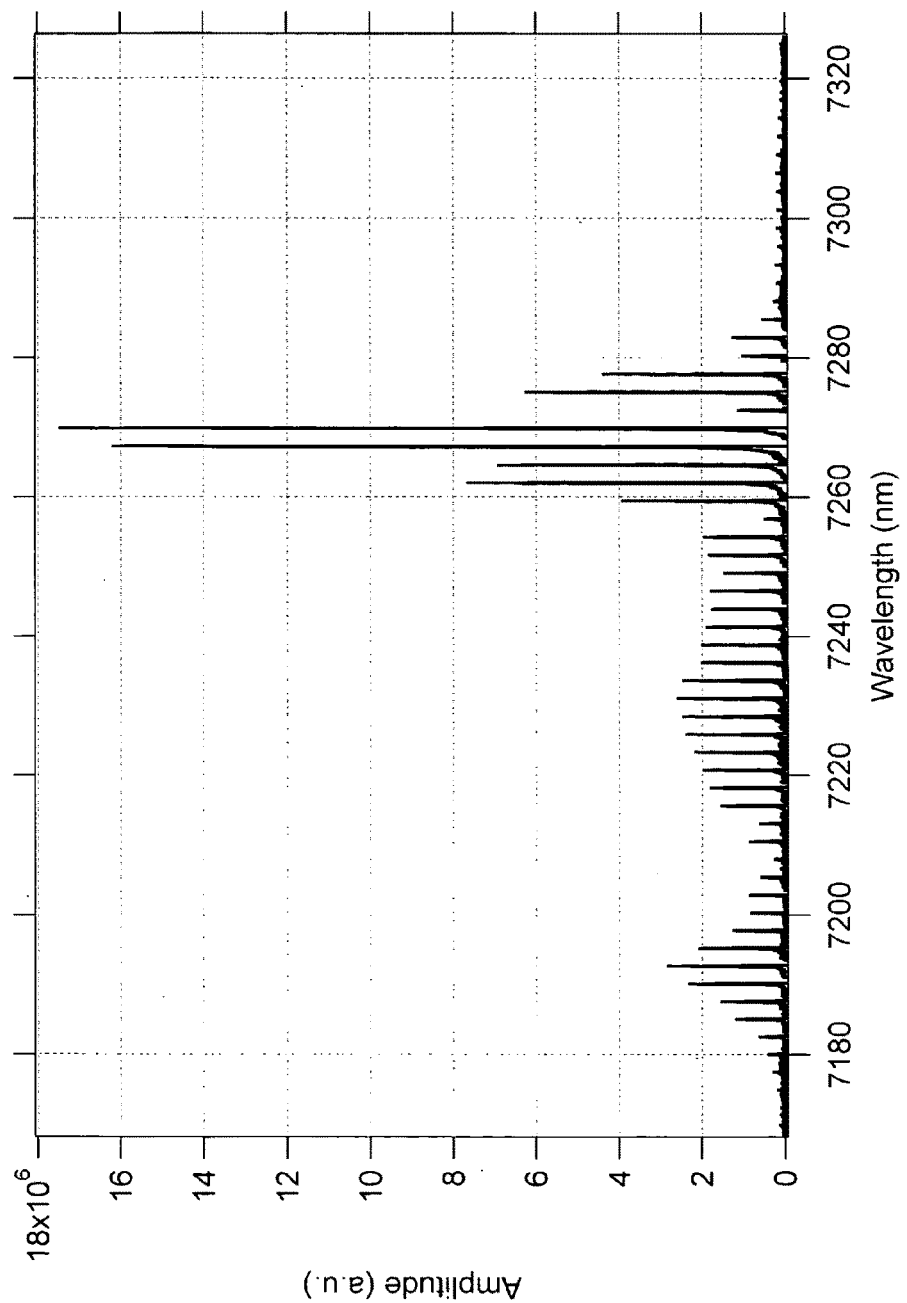
FIG. 1 is a diagram of an output spectrum of the Fabry-Perot geometry 7.3 μm QCL.

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

The masculine pronoun is generally used herein to indicate the generic individual and as a matter of convention and convenience.

The present invention resides in several embodiments.

In one embodiment of the present invention, a method for leveling the output of a multiwavelength laser system over a number of lasing wavelengths in a tuning window is set forth with the steps including the providing a laser gain chip and determining a first current change value needed to shift the laser gain chip's FP mode comb exactly one free spectral range. The laser system is then tuned with monitoring occurring for a second current change value from the initial point during the tuning. Remapping then occurs with the remapping of the second current change to the first current change when the second current change exceeds the first current change. Remapping takes place by subtracting the second current change from first current change such that laser output power varies minimally with laser wavelength as the second current change value for a tuned wavelength of the multiwavelength laser system is remapped onto the first current change value.

In another embodiment, a laser illumination system for providing laser light over a multiwavelength spectrum includes a multiwavelength laser light source emitting light and a wavelength-selective reflector in optical communication with the source. A translator coupled to the reflector displaces the reflector according to a first signal and controls a distance between the reflector and the source. A rotation stage is coupled to the translator. The rotation stage rotates the reflector according to a second signal and controls an angle between the reflector and the source such that single mode, continuous, mode-hop free tuning is provided by the laser illumination system.

In a third embodiment, a method for more quickly determining the presence of a target gas includes the steps of identifying and selecting regions in a frequency range of a selectable wavelength light source which meets all the following criteria: the target gas has large absorption in at least some frequencies in the frequency range, expected interferents have low absorption at their expected concentrations, and a detectable signature of the target gas is linearly independent of signature of interferents. A sample of gas is collected for testing of the target gas and a scan is performed across the identified and selected regions with the collecting of photoacoustic data from the scan. The photoacoustic data is linearly deconvolved against a standardized library of the target gas and list of expected interferents to obtain a gas concentration measurement for the target gas.

Referring to the drawings, where like numerals of reference designate like elements throughout, it will be noted that at least three key innovations are provided the technology disclosed herein.

The first is a software-implemented algorithm (or method) that provides tuning capability of the single wavelength QCL output such that under computer control, the laser wavelength can be reproducibly tuned over a very broad spectral region without experiencing any mode hops or jumps. The computer simultaneously controls the QCL drive current, the angle of the wavelength selective grating and the over-all cavity length. Furthermore, an all-mechanical system is provided that automatically and in a highly-coordinated fashion provides the cavity length adjustment as the angle of the grating is changed. When performed in tandem, these coordinated actions enable selection of the desired operating wavelength of the QCL.

Second, a laser wavelength tuning algorithm/method is achieved by creating a "Smart Grid" of interrogating wavelengths that simultaneously focus on the unique features of the fingerprint absorption of the desired targets while eliminating those wavelengths at which the key interferents may have their sharp absorption features. Use of appropriate Smart Grids improves the ROC (receiver operational characteristic) curves, i.e., the characteristic describing the detection threshold versus probability of false alarms and reduces the time it takes to make a measurement.

Third, performance optimization of the tunable QCL based trace gas detection scheme is achieved by iteratively changing the measurement algorithms in a learning mode as the instrumentation carries out the trace gas detection.

Broad Tuning of Single Wavelength Quantum Cascade Lasers

A QCL with no additional controls, other than the reflectivity provided by the end-facets, acts as a Fabry-Perot laser that lases on the longitudinal modes of the laser cavity formed by the two end facets (assuming that the lateral dimension of the gain region is small to support only one transverse mode). All the longitudinal modes falling under the QCL gain curve and for which the QCL gain exceeds the cavity round trip losses, could lase to create laser light, producing a comb of laser wavelengths separated by the longitudinal cavity mode spacing (FIG. 1).

To go from the multiwavelength output shown in FIG. 1 to a single wavelength output that is necessary for the measurement of the fingerprint absorption of the target gases, a wavelength selective loss element needs to be incorporated within the QCL cavity. The simplest such wavelength selective element is the incorporation of a distributed feedback (DFB) grating in the active layer of the QCL. Such DFB lasers do provide single wavelength output at the grating wavelength. However, tunability of the laser wavelength is limited and is provided by temperature changes of the QCL (which also changes the refractive index and the grating dimensions). Typically, DFB laser wavelength tunability is limited to about 20-30 nm, far less than what would be needed for interrogating a target gas whose absorption feature(s) may span hundreds of nanometers (nm). Broad tunability, necessary for trace gas detection, is obtained by having a wavelength selective component that is external to the QCL. Such configuration, in the infrared region, uses an external reflection from a diffraction grating in Littrow (or other) configuration. In the simplest analysis, the angle of the grating with respect to the laser axis determines the lasing wavelength.

In a general case, an external grating cavity (EGC) tunable semiconductor laser consists of a gain chip and a wavelength-selective element optically coupled to one of the facets of the gain chip. In a system with no AR (anti-reflective) coatings on the gain chip facets as the most general case, one encounters the well-described coupled cavity problem. This produces single-mode output radiation and to wavelength-tune such a system continuously, the longitudinal modes of the gain chip have to match those of the external cavity and the loss minimum of the wavelength selective element. Therefore, such a system has to have three controls to change all parameters independently.

The external cavity configuration described above is very complex due to the necessity to control three (3) parameters synchronously, namely 1) the wavelength grating angle selection, 2) the overall cavity length, and 3) the gain chip's FP (Fabry-Perot) mode comb. In addition to the mechanical and electronic complexity that negatively affects reliability, such configuration exhibits several performance-based negative characteristics which are all constructively addressed by the system and methods disclosed herein.

First, since the FP mode comb of the gain chip is adjusted by changing the laser drive current (or alternatively by adjusting gain chip temperature), it is impossible to avoid output power changes as the laser tunes. This can be undesirable for some applications. Further, the tuning process is slow due to the adaptive nature of the novel tuning algorithm/method set forth herein that finds external cavity modes by tuning its length and finding power maxima.

One simplification to the system results from the elimination of the gain chip's FP etalon effect, which can be achieved by applying a high performance (<<1%) antireflection (AR) coating to the output facet of the gain chip facing the external cavity. With an AR-coated gain chip, the requirement to match the modes of the external cavity to those of the gain chip is eliminated, and therefore only two controls remain—the wavelength selection, and the overall cavity length control to align a given EC (external cavity) longitudinal mode with the loss minimum of the diffraction grating.

In an external cavity configuration utilizing a diffraction grating as the wavelength selective element, grating angle is controlled mechanically. Cavity length can be controlled (1) via change of physical length, (2) optical control via refractive index change, or (3) a novel mechanical control.

Optical cavity length control relies on the change in the optical path length of the overall cavity via changing the refractive index of one or more intracavity components without changing its physical length. Numerous such schemes have been developed over the years, including the use of separate electro-optic crystals, fabrication of integrated electro-optical modulators adjacent to the gain chip, etc. Since electro-optics for the mid-IR and far IR is in its infancy, methods for optically changing the overall cavity length via changes to the refractive index of the gain chip itself are set forth herein.

Gain Chip Current Control: Periodic Current or Temperature Tuning

A well-known approach to changing the refractive index of the gain chip is changing the injection current or gain chip temperature, thus taking advantage (indirectly or directly) of the refractive index's temperature dependence.

However, this approach contains a serious limitation on the overall tuning range, namely the limited dynamic range of the laser gain chip control parameters, including laser injection current and temperature. For some typical QCL gain chips, the total current span between laser threshold and the maximum rated laser current is only sufficient to shift the FP comb by less than 3 cm$^{-1}$, thus putting an upper limit on the mode hop-free tuning range. In a practical instrument, where a reasonably high laser power level needs to be maintained in order to achieve the desired sensitivity, the actual tuning range becomes less than 1 cm$^{-1}$. Practicably attainable gain chip temperature range imposes a similar tunability restriction.

The problem posed by this limitation has been overcome by inventing the algorithm/method set forth herein where the current (or temperature) is periodically changed to maintain high power operation.

First, determination is made of the current change value need to shift the gain chip's FP mode comb exactly one free spectral range, which will be called hereafter the current periodicity value.

This could be achieved, for example, by analyzing high resolution FTIR (Fourier transform infra-red) spectra of the gain chip in FP configuration at varying injection currents, or by spectroscopic means as described below with respect to the experimental demonstration.

Next, as the laser begins tuning, the algorithm keeps track of the current value change from the initial current set point. When that change exceeds the previously determined current periodicity value, the algorithm subtracts that value from the next desired set point, and thus remaps the current change span back onto the original region of operating current. If one sets the maximum allowed current as the upper bounding value, this results in the highest average output power across the tuning window.

Further, the same approach can be employed if one uses gain chip temperature instead of the injection current as the control parameter for refractive index. However, temperature is typically much slower to respond, making current control the preferred embodiment.

Finally, the periodic current/temperature change algorithm is independent of whether one desires a true continuous tuning (where the overall cavity length needs to be changed with spectral tuning to maintain the selected FP mode of the external cavity at the minimum of loss), or quasi-continuous tuning of an intentionally long cavity where mode hops over external cavity modes are acceptable.

Gain Chip Current Control: Harnessing Saturation

Any standard gain chip index control method, including periodic current control described above, has the undesirable property that the output power of the laser varies with the change of the wavelength. This property is undesirable for many applications, where constant output power needs to be maintained as the laser is tuned. A method that minimizes such changes through the use of the power saturation region of the light-current (LI) curve characteristic of QCLs may be used to resolve this problem.

Figure 2:
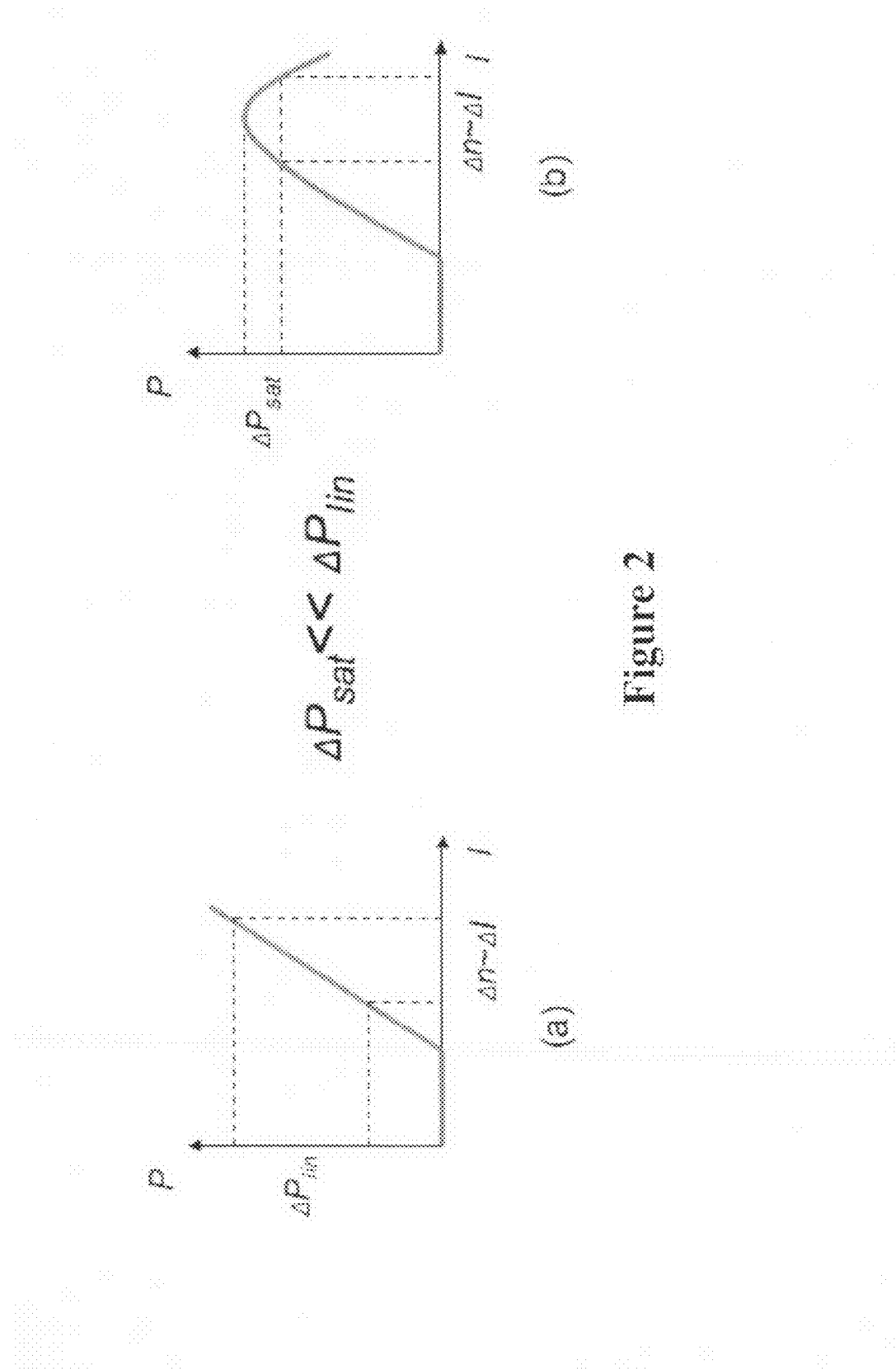
FIG. 2 is a diagram of light-current (LI) characteristics of semiconductor lasers: a) in the standard, linear operating regime; and b) in the operating regime utilizing power saturation.

FIG. 2 illustrates this concept. FIG. 2a shows the standard operating regime for controlling gain chip refractive index with injection current. Since one uses the linear portion of the LI, there is an appreciable change in output power ($P_{lin}$) as one varies the index by the needed amount. However, QCLs are characterized by a noticeable saturation portion of their LI curves. Saturation is caused by either thermal effects or by electronic band misalignment under higher bias conditions, and is reproducible and completely reversible. Therefore, one is free to select the laser operating point to minimize optical power changes for the same change of current (FIG. 2b). It is obvious that the "saturation power change" is much less than in the linear case ($P_{sat} << P_{lin}$).

A QCL gain chip for this application may be specifically designed to exhibit a saturation region that is as flat as possible since this will minimize optical power changes. In the ideal case of a completely flat saturation region (which we have already observed in some devices), the optical power change with laser tuning in this configuration is effectively eliminated.

Gain Chip Current Control: 2-Segment QCL

Even if the saturation region of the gain chip's LI curve cannot be made completely flat, we have devised a system where the total output power can be kept constant as the refractive index is changed via changing the current.

Figure 3:
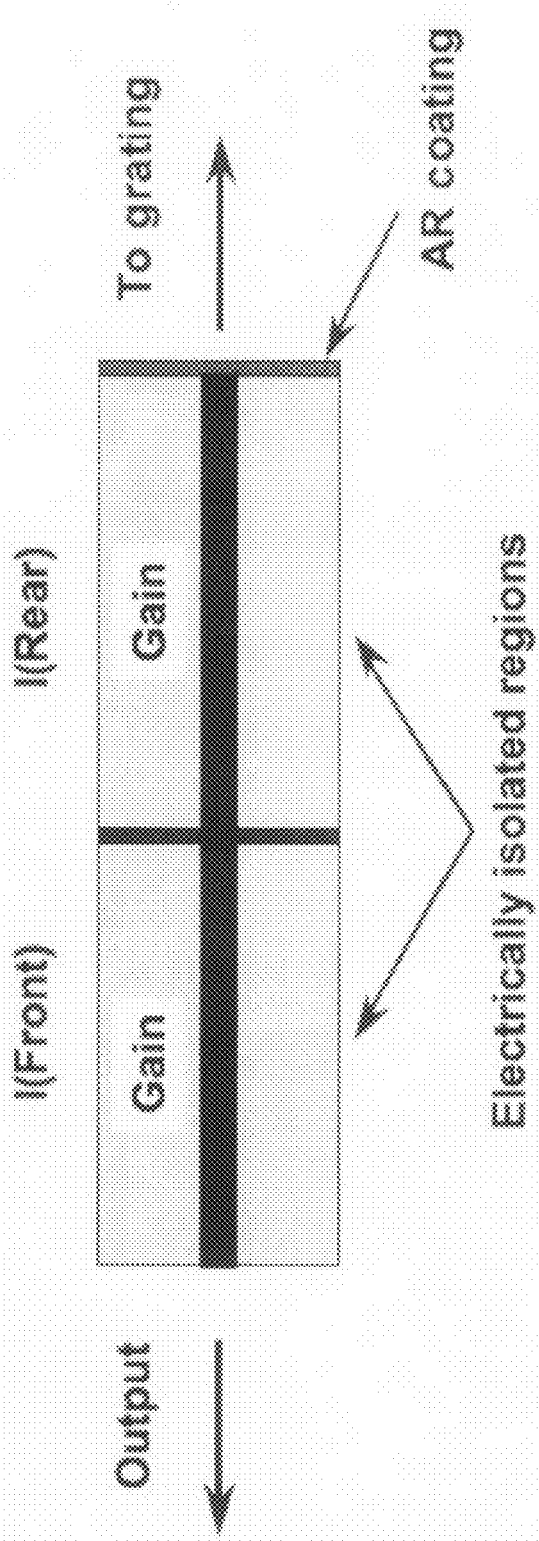
FIG. 3 is a labeled schematic of a two-segment QCL chip.
Figure 4:
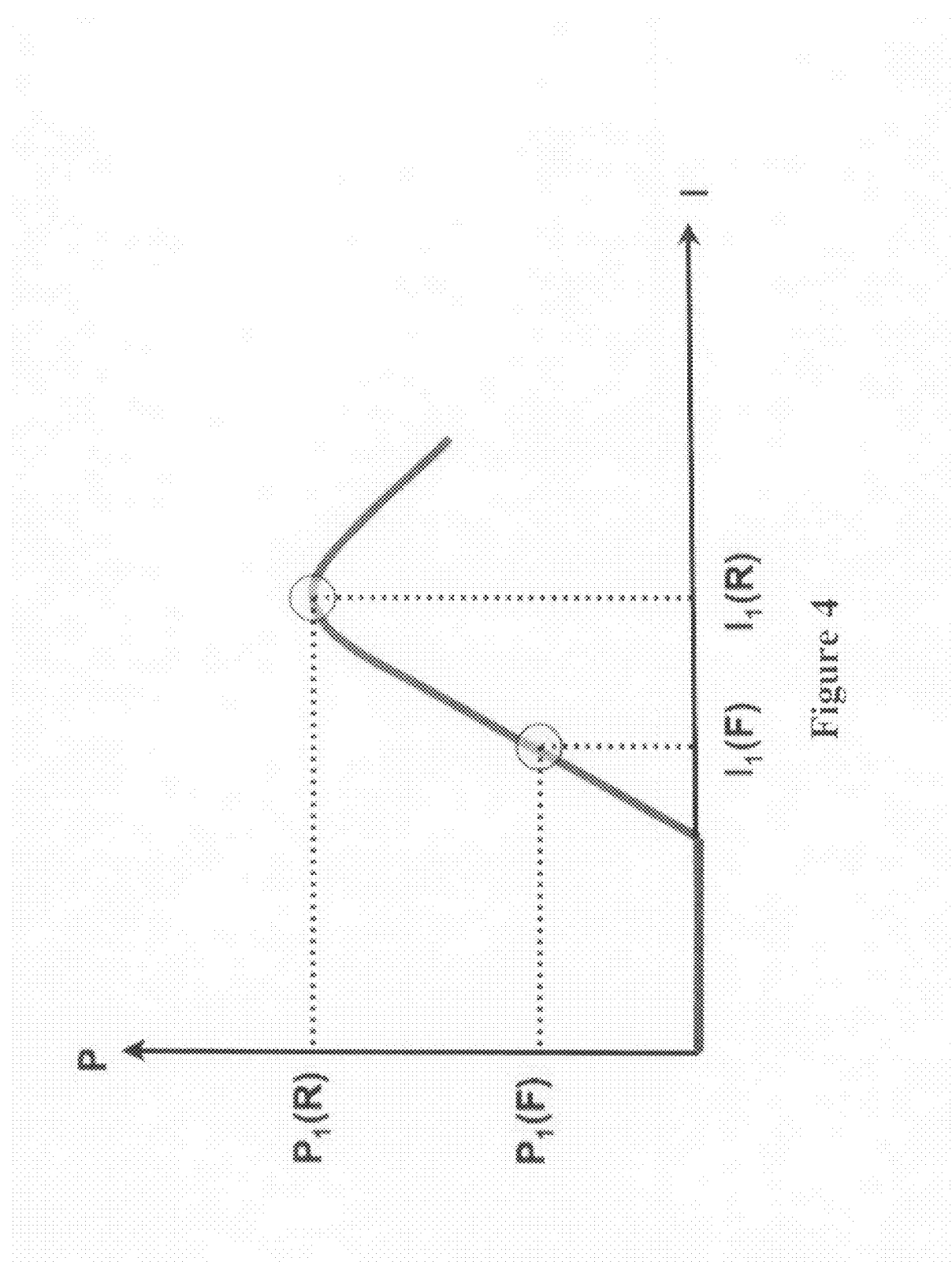
FIG. 4 is a diagram showing operating point 1 of a two-segment QCL such as that shown in FIG. 3.
Figure 5:
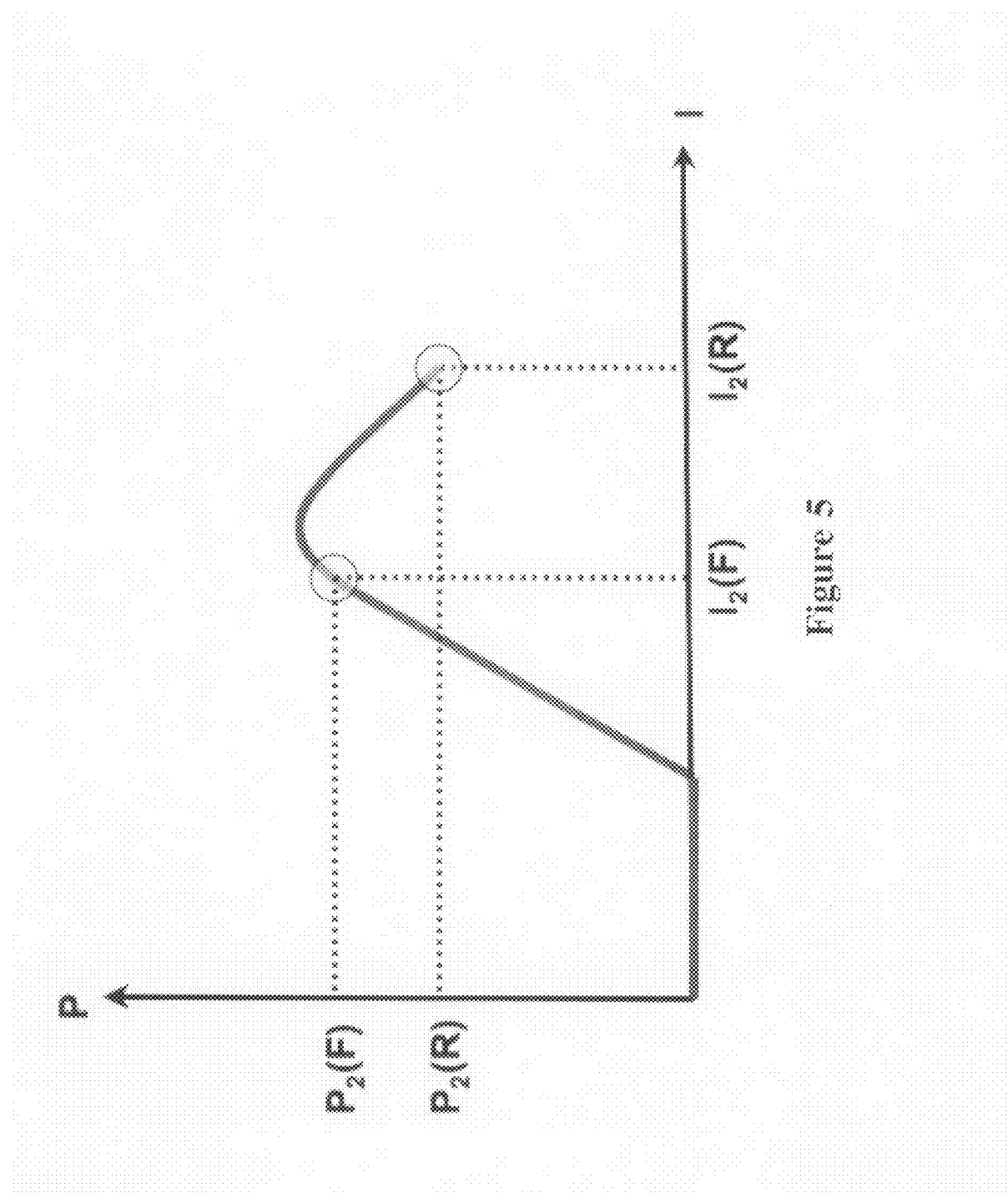
FIG. 5 is a diagram complementing that of FIG. 4 showing operating point 2 of a two-segment QCL.

FIG. 3 shows a single QCL chip with 2 independently addressable electrical contacts. The operating points of the two (2) sections may be chosen to be on the opposite sides of their respective maximum power points of their LI curves (FIG. 4). Then, as the laser is tuned, the current of both sections is increased so that the front section moves closer to the maximum power point, and the rear section moves away from it (FIG. 5). The total current through the device will be increasing, thus monotonously changing the refractive index of the two (2) sections, and therefore properly varying the overall cavity length. However, due to the existence of optical power saturation, the optical power of the front section will increase, while that of the rear section will decrease. The size of the respective current changes can be selected such that the overall optical power is kept constant as the laser is tuned (Equations 1 and 2).

$$I_1(F)+I_1(R)>I_2(F)+I_2(R) \quad (1)$$

Therefore, the refractive index, n, changes. However, $$P_1(F)+P_1(R)>P_2(F)+P_2(R)$$

$$P_{output}=\text{const} \quad (2)$$

In this configuration, the total optical power is lower than if both sections were tuned around the maximum optical power point (which in effect is equivalent to the previous solution, titled "Harnessing Saturation"). Therefore, such a 2-segment QCL provides operational flexibility where one can either tune the laser source with constant power at a somewhat lower overall level, or accept power variations and generate maximum possible power at every spectral point.

Finally, even though described for the case of a QCL, this invention will be applicable to any semiconductor laser that exhibits such reproducible and reversible power saturation with increased current.

Gain Chip Current Control: Power Equalization Across the Gain Curve with the 2-Segment QCL Output power change due to the variation in injection current necessary to change the overall external cavity length (addressed immediately above) is one of the two main mechanisms responsible for output power variation as the laser source is broadly tuned. The second mechanism is the decrease of the laser gain as one spectrally tunes the source away from gain maximum, towards the edges of the tunability window.

Using the 2-segment QCL approach, this second source of power variability can also be suppressed, and in some cases completely eliminated, depending on the actual characteristics of a given system (namely, the shapes of the gain and LI curves). This will be accomplished by changing the spread (or current difference) between the current setpoints of the two QCL sections. The spread value controls the total output power at any given setpoint. The lower the spread, the higher will be the total power. Therefore, as the laser is tuned away from the center of its gain curve, the spread will begin to decrease in order to compensate for the decrease in gain by pumping the laser harder.

The extent to which this method will be able to stabilize output power depends on the actual system characteristics. On the other hand, this approach gives the system designer wide flexibility in selecting system operating modes and parameters, allowing the tradeoff between maximum output power and maximum power stability, as well as allowing tailoring of the actual dependence of power on wavelength to suit any particular application.

Experimental Demonstration of Computer Control of QCL Wavelength Through Simultaneous Control of the Grating Angle, QCL Current And Cavity Length In our case, a quantum cascade laser (QCL) gain chip was incorporated into an external grating cavity (EGC) to produce single mode continuous mode hop free tuning. The 7,300 nm QCL epi material was grown using molecular-beam epitaxy. After cleaving, the 3-mm-long, 10.6-μm-ridge-width chips were mounted epi-side down on an AlN (aluminum nitride) substrate by using Au—Sn (gold-tin) eutectic solder. The chip on the submount was integrated onto a copper heat-spreading pyramid with a thermoelectric cooler (TEC) and a miniature copper cooling block for heat removal from the hot side of the TEC. The cooling block is water-cooled but can be modified for forced-air cooling. The gain chip was operated at an actively controlled submount temperature of 25° C., measured by an integrated thermistor, with the copper cooling block maintained at 20° C.

Operated in Fabry-Perot (FP) geometry, the 7,300 nm QCLs (uncoated facets) generated multimode continuous wave (CW), room temperature (RT) power output of 80 mW per facet. See FIG. 1 for a spectral analysis of the output.

To collimate the input and output beams, two collimator lenses were used. The collimators were ZnSe (zinc selenide) aspheric, 6 mm diameter, f/0.7 lenses with 5500 to 7300 nm AR coatings. The output beam from the collimator was approximately 4 mm in diameter.

Figure 6:
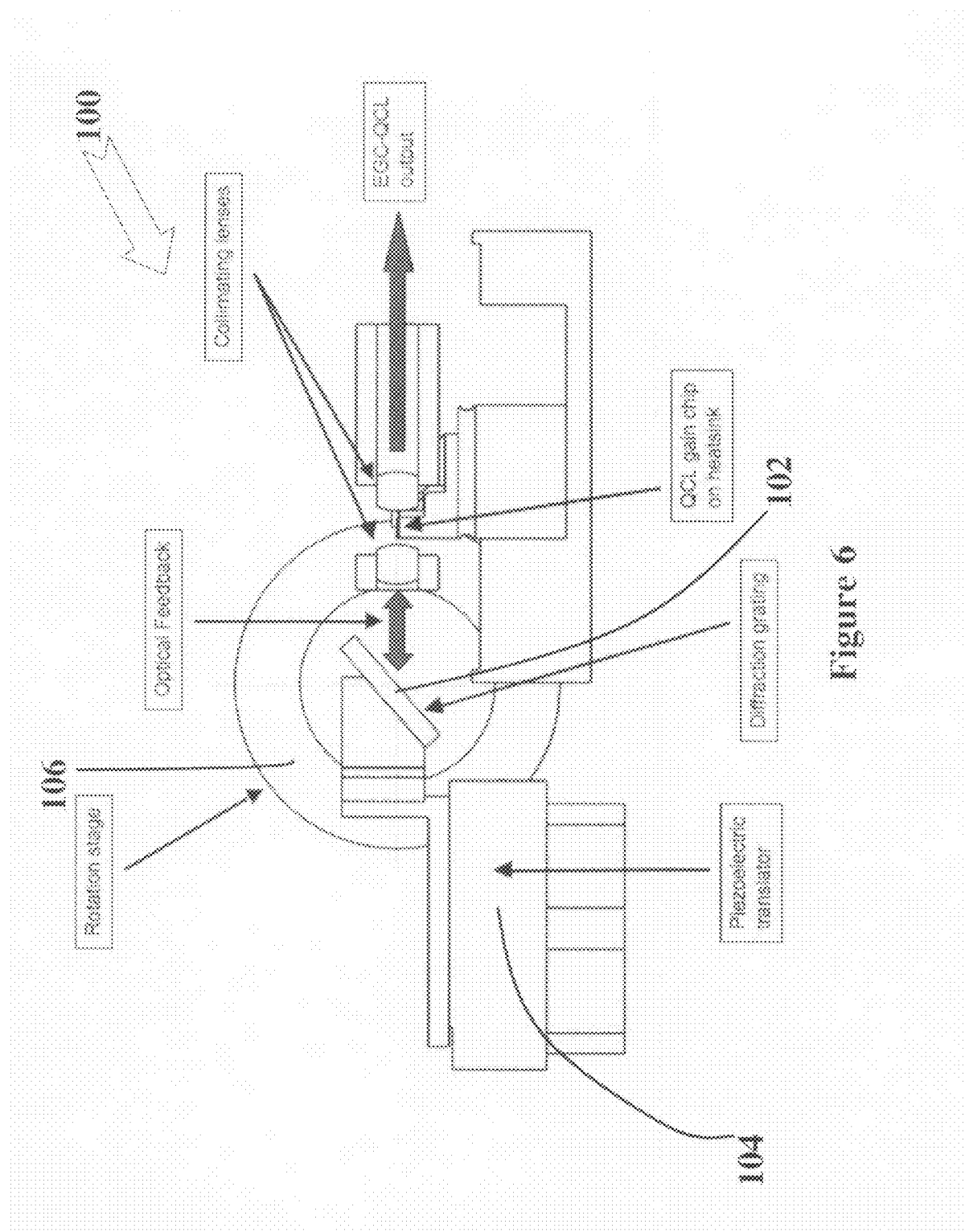
FIG. 6 is a cross-sectional view of the external grating cavity quantum cascade laser (EGC-QCL) system described herein.

FIG. 6 shows a cross-sectional view of the EGC-QCL (external grating cavity—quantum cascade laser) system 100.

The external cavity included an output laser facet with no coating and a diffraction grating 102 with 240 grooves/mm as a second mirror and wavelength selective element (FIG. 6). Alignment quality of the EGC is judged by the strength of feedback it provides to the gain chip, measured by threshold current reduction. For the 7300 nm laser described here, threshold current dropped from 850 mA in FP geometry to 730 mA in EGC configuration (14% reduction). The entire setup was enclosed into a plastic box and filled with dry nitrogen to prevent water absorption inside the external cavity, which is strong in this spectral region.

The aforementioned diffraction grating 102 was mounted on a piezoelectric translator (PZT) 104 which is computer controlled by changing the piezo voltage and capable of approximately 30 μm linear displacement. The PZT 104 controls the length of the external cavity by moving the grating 102 along the optical axis. Change of external cavity length allows control of the external cavity modes. The grating-PZT assembly is in turn mounted on a computer-controlled rotation stage 106. This control provides the overall wavelength selection by changing the grating angle and thus controlling the frequency that is reflected back to the gain chip.

Between the grating-PZT assembly and the rotation stage 106, both the external cavity modes and the overall wavelength selection can be independently controlled in a coordinated fashion.

The single pass external cavity length for our system was approximately 4 cm, yielding an external cavity mode spacing of around 3.75 GHz (0.125 cm$^{-1}$). Gain chip modes are roughly 15 GHz (0.5 cm$^{-1}$) apart. Since our lasers did not have AR coatings, the system exhibited coupled cavity behavior. Therefore, it required three controls to ensure single mode, continuous, mode-hop free tuning. Gain chip current controls its FP mode comb, grating angle controls center wavelength, and PZT controls external cavity FP mode comb. To have reproducible single mode operation, the desired gain chip mode has to be aligned with the proper external cavity mode and with the central wavelength of the diffraction grating. After all modes are aligned properly, an FTIR scan has to be performed to measure wavelength at given control positions. To tune such a system continuously, starting from this pre-aligned point, chip current, PZT displacement and grating angle should be changed simultaneously and in a synchronized fashion.

To align all modes in the first place, the following approach was developed. Laser current is set to its maximum value, and then the grating angle is scanned with a fine step across the entire gain curve (allowed spectral output region) of the chip.

For each grating step, the PZT scans the distance equal to a few wavelengths, and system output power is continuously measured. After the PZT ramp is finished, maximum value of power is recorded. After that, the grating moves to next step. As a result of such a scan, a curve with distinct, periodic power maxima and minima with changing wavelength is acquired. Each maximum position of the curve corresponds to a best match between grating angle, EC length, and gain chip current.

From the spectral positions of these maxima, the law of grating movement for single mode continuous tuning is determined by a polynomial fit:

$$GP = GP_0 + A(v - v_0) + B(v - v_0)^2 \quad (3)$$

where GP—grating angle position (mm) at a desired frequency v (cm$^{-1}$), $GP_0$—starting grating position (mm) at starting frequency $v_0$ (cm$^{-1}$), A and B—polynomial fit coefficients.

The equation for chip current change is:

$$I = I_0 - \Delta I_{FSR} \frac{v_0}{v} \mathrm{mod}\left(\frac{v - v_0}{\Delta v_{FSR}}, 1\right) \quad (4)$$

where $I_0$—starting/maximum current (mA), $v_0$—starting frequency (cm$^{-1}$), v—frequency (cm$^{-1}$) at the current I (mA), and $\Delta I_{FSR}$—current change (mA) necessary to shift the gain chip's Fabry-Perot comb by exactly one free spectral range ($\Delta v_{FSR}$ cm$^{-1}$) in the vicinity of $v_0$.

The PZT 104 finds its position adaptively by finding maximum power at each point of the scan. As one can see from the expression for current, every time the frequency moves one free spectral range of a chip, the current jumps back to maximum value and then starts going down with the frequency. This type of periodic current tracking, described above, allows us to remove the output power dynamic range limitation that would otherwise be imposed on the tunability window, and to maintain high output power across the entire gain curve of the chip. For the laser described above, $\Delta I_{FSR} = 60.8$ mA and $\Delta v_{FSR} = 0.49189$ cm$^{-1}$ at $I_0 = 1294.4$ mA. The $v_0/v$ term corrects for the fact that the Fabry-Perot comb does not really shift but rather expands the comb from zero frequency.

The free spectral range of the gain chip, $\Delta v_{FSR}$, can be determined by taking a high resolution FTIR scan of the gain chip in FP configuration and measuring the distance between adjacent modes. We have devised two independent ways of determining $\Delta I_{FSR}$. One way is to take FTIR scans of the gain chip in FP configuration for different currents and linearly fit data. A second approach is to utilize a photoacoustic gas cell and manually find a reference gas line by adjusting grating angle and gain chip current to obtain maximum photoacoustic signal. During this process, the PZT should be constantly moving to average out the effect of the external cavity mode mismatch. After an absorption line is found and optimized, the grating angle stays constant and the laser current is changed until the photoacoustic signal is maximized again, which means that current was shifted exactly one FSR (free spectral range).

Figure 7:
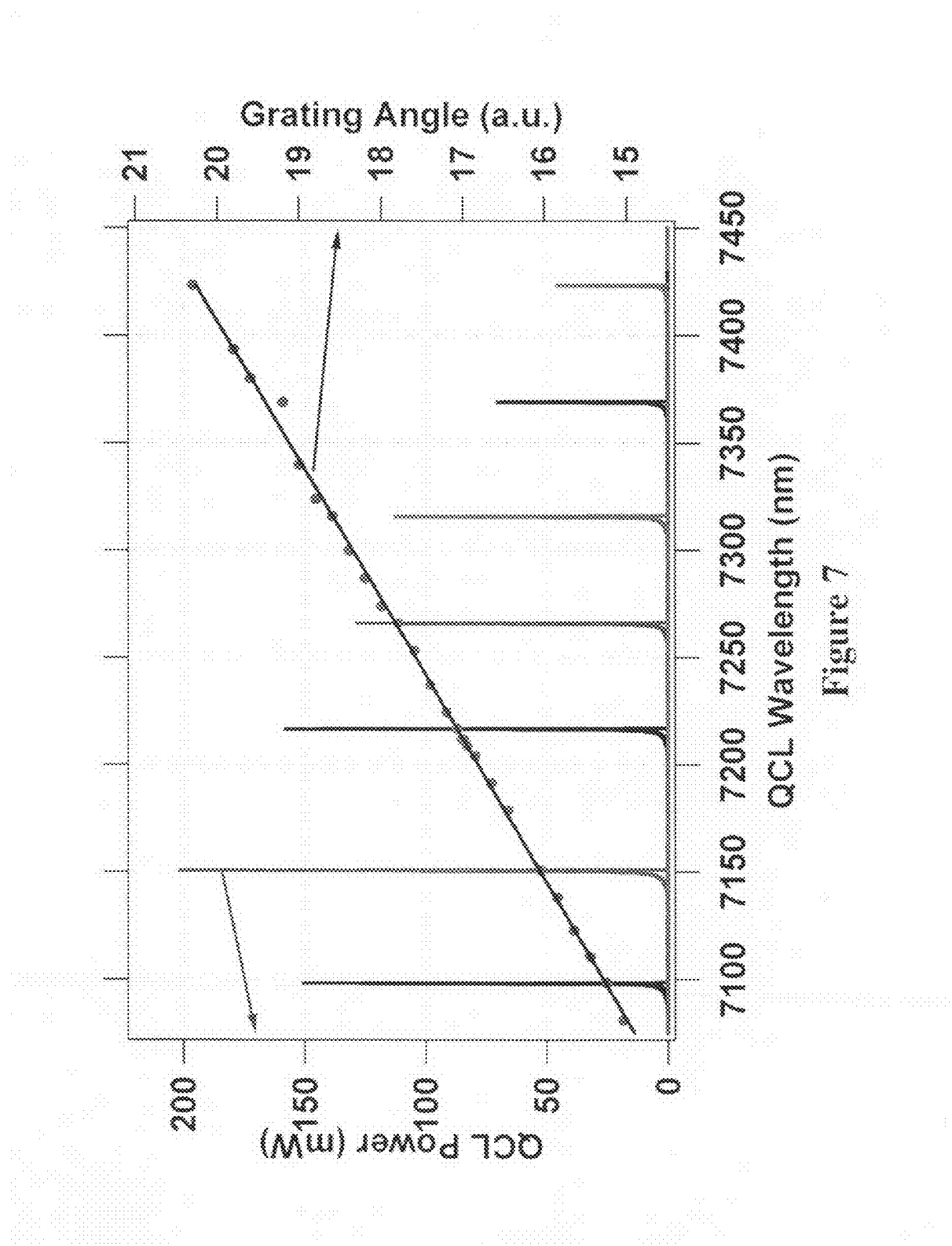
FIG. 7 is a diagram showing tuning characteristics of continuous wave room temperature operation of the 7.3 μm EGC QCL.
Figure 8:
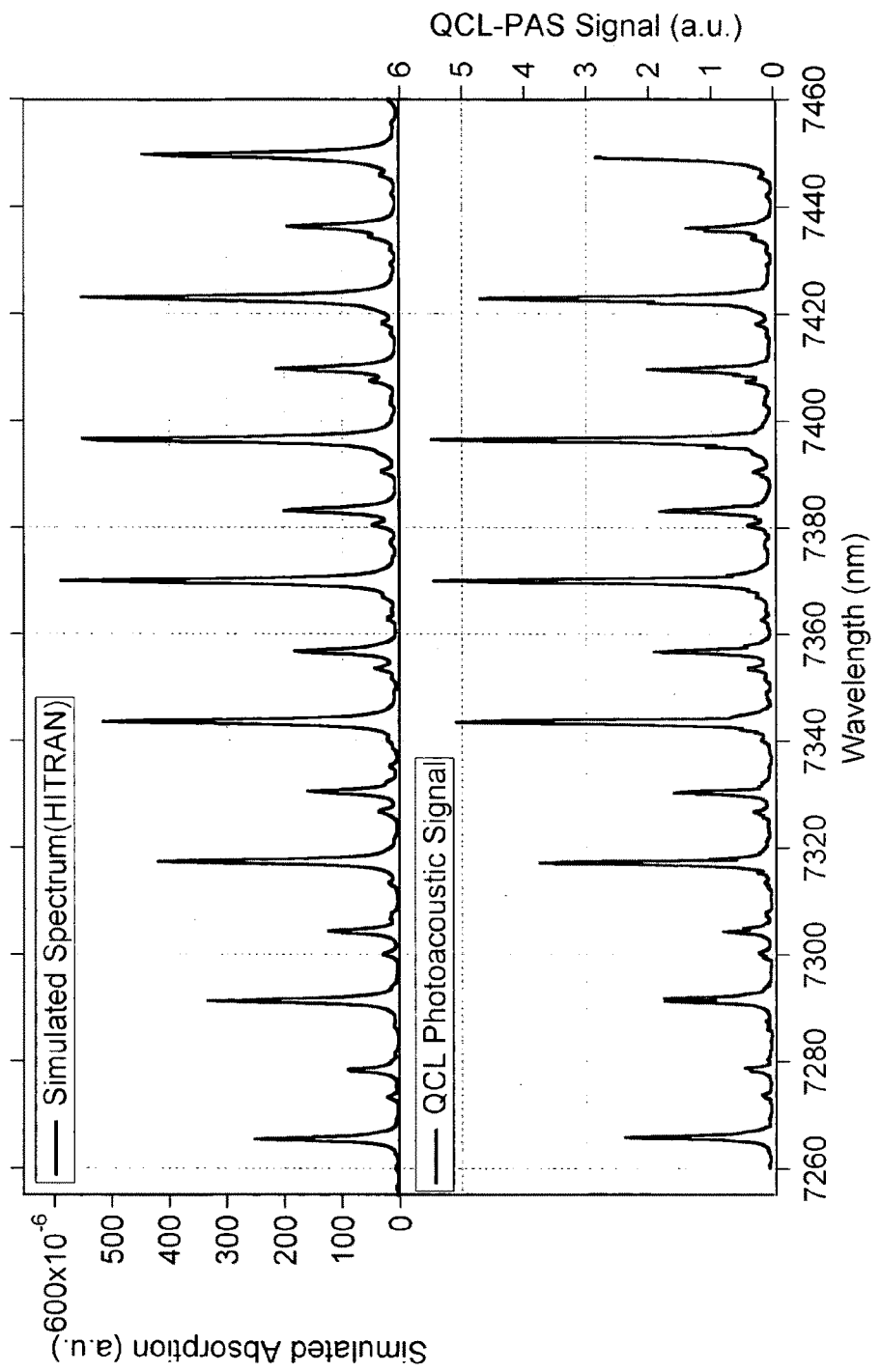
FIG. 8 is a comparative diagram showing high resolution HITRAN simulated absorption spectrum of acetylene (top trace) and measured QCL-PAS spectrum of 10 ppm acetylene in CDA at a total pressure of 300 torr (bottom trace).
Figure 9:
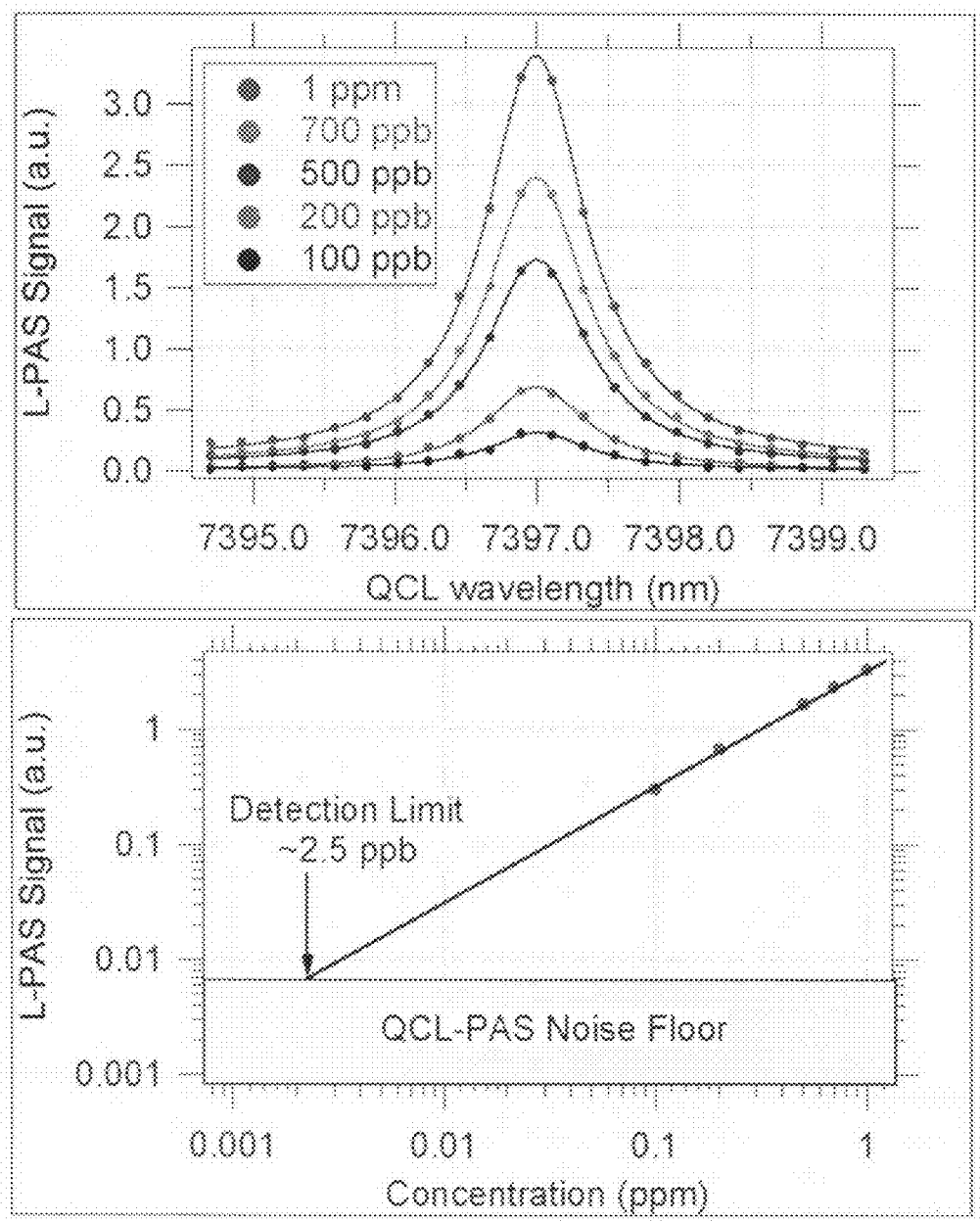
FIG. 9 is a coordinated diagram showing acetylene L-PAS measurements as a function of acetylene concentration. The figure also shows the lowest detectable of level for acetylene detection.

For our short cavity setup, we obtained an overall tuning range of 350 nm, centered around 7,350 nm with highest single frequency optical power of nearly 200 mW (FIG. 7). At the edges of the gain curve, laser output goes to Fabry-Perot mode even in the presence of feedback. A proof of continuous single mode, mode hop free tuning over 200 nm range and of the very narrow output linewidth while tuning was obtained by measuring PAS (photoacoustic spectroscopy_spectrum of 10 ppm acetylene in 750 Torr of CDA (clean dry air) (FIG. 8). The near perfect match between the measured line positions and linewidths and those obtained from HITRAN simulations, provides convincing proof that computer-based algorithm provides a mode hop free tuning system even with an uncoated facet QCL gain chip. By carrying out QCL-PAS on one of the features of acetylene as a function of the partial pressure of acetylene, we obtained the minimum limit for the detection of this trace gas (FIG. 9) of 2.5 ppb.

As of the filing date of this patent, the website at http://cfa-www.harvard.edu/hitran// (aliased by www.hitran.com) indicates that HITRAN is an acronym for high-resolution transmission molecular absorption database. HITRAN is a compilation of spectroscopic parameters that a variety of computer codes use to predict and simulate the transmission and emission of light in the atmosphere. The database is a long-running project started by the Air Force Cambridge Research Laboratories (AFCRL) in the late 1960's in response to the need for detailed knowledge of the infrared properties of the atmosphere.

The system described above has three controls for single mode continuous tuning. However, one can remove the need for PZT control for by relaxing the continuous tuning requirement. To achieve that, instead of short cavity, a long cavity can be used. In this case, laser tunes quasi continuously, on a grid determined by the positions of the FP comb of the external cavity. The spectral density of the grid is determined by the overall optical length of the external cavity, and laser will hop from one external cavity mode to another while tuning. If the spectral distance between external cavity modes is much smaller than the characteristic width of a spectroscopic feature studied, the laser source can be treated as continuously tunable.

In our long cavity system, a room temperature QCL with the gain region centered at 6.3 μm was mounted and operated in the manner similar to that described above. Chip length was 4 mm and crystal facets were not coated.

The output from the back facet of the gain chip was collimated by using either a f/1.0, 25-mm diameter off-axis parabolic mirror or a f/0.7 aspheric AR coated ZnSe collimating lens. Beam diameter of collimated beam in the case of a parabolic mirror was roughly 2.5 mm and in the case of ZnSe lens was roughly 4 mm. The resulting collimated beam was reflected off a planar, 300 grooves-per-mm diffraction grating blazed at 5.4 μm. In the case of the parabolic mirror, the grating was mounted in the Littrow configuration. In case of the ZnSe lens, the grating was mounted in a double pass configuration where the beam was reflected from the grating and incident on a flat mirror to be reflected back to the grating and then to the gain chip. Such configuration lets us compensate for the decrease of grating resolution due to beam size reduction. The length of the external cavity in both cases was maintained at around 100 cm, yielding FP mode spacing of approximately 150 MHz. Gain chip mode spacing was approximately 12 GHz. Resolution of the grating was sufficient to support single mode tuning over the range of ~350 nm. The single mode CW output power in the center of gain curve at the maximum current was around 300 mW (FIG. 10).

In the long cavity configuration, only two parameters need to be controlled simultaneously in order to achieve single mode tuning of the system. One parameter is laser current, the other parameter is grating angle. Grating angle is controlled by a linear actuator driving a rotation stage, as described above. Grating angle and current change algorithm were the same as described for the short cavity case.

Figure 10:
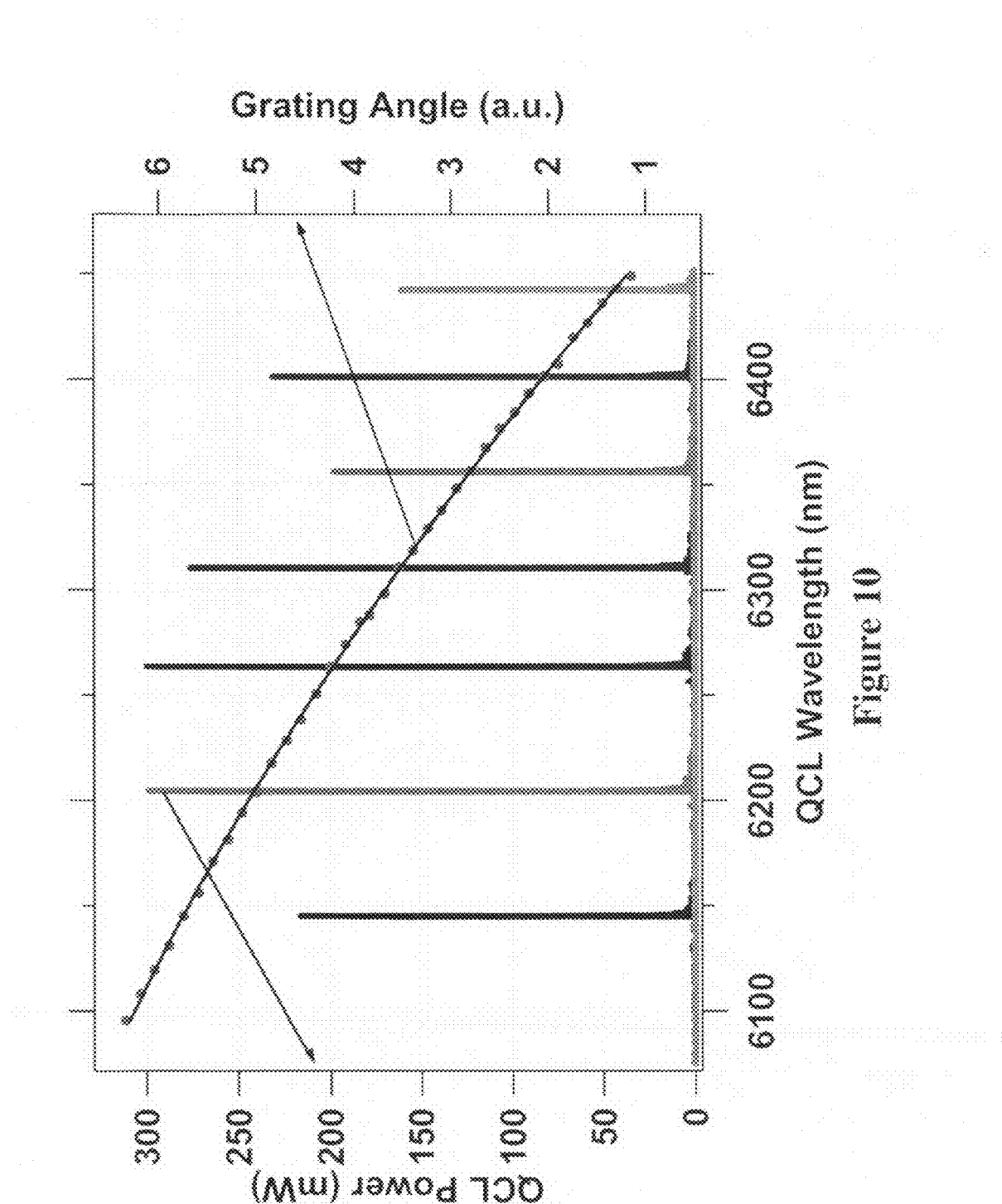
FIG. 10 is a diagram showing tuning characteristics of continuous wave room temperature operation of the 6.3 μm EGC QCL. The highest measured single-mode power is ~300 mW.

We obtained an overall tuning range of 350 nm centered at 6,300 nm with maximum single frequency optical power of 300 mW (FIG. 10). Continuous tuning was demonstrated by recording actual gas spectra over approximately 20 nm range with absolute frequency error of no more than 1 GHz. Further continuous tuning was confirmed by recording FTIR spectra in several additional randomly selected regions of the overall tuning window, spanning multiple free spectral ranges of the gain chip.

Figure 11:
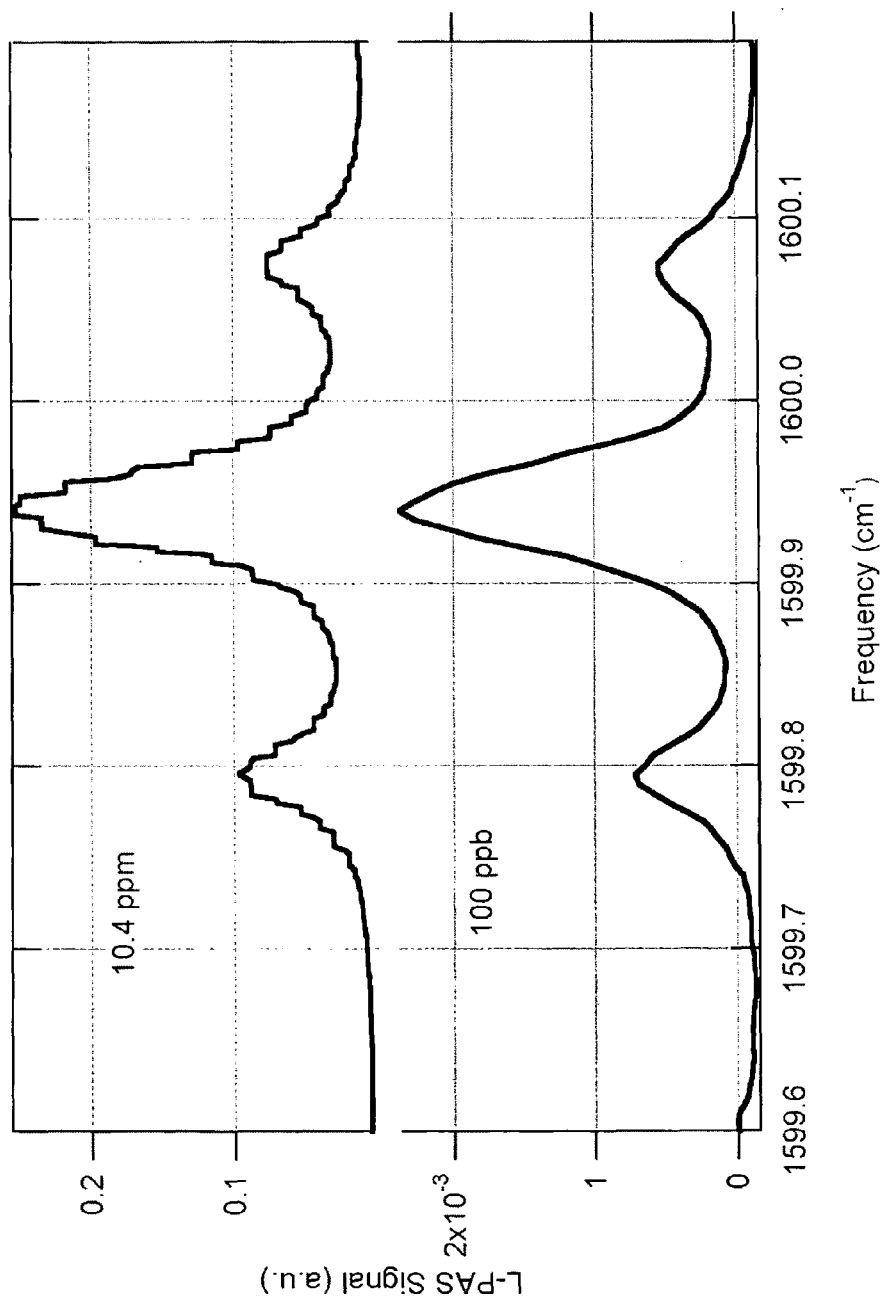
FIG. 11 is a comparative diagram of L-PAS scans across the selected $NO_2$ spectral feature in clean dry air. The top trace shows 10.4 ppm $NO_2$ and the step changes in the signal intensity are due to external cavity mode hops. The bottom trace shows five-point averaged 100 ppb $NO_2$ data.
Figure 12:
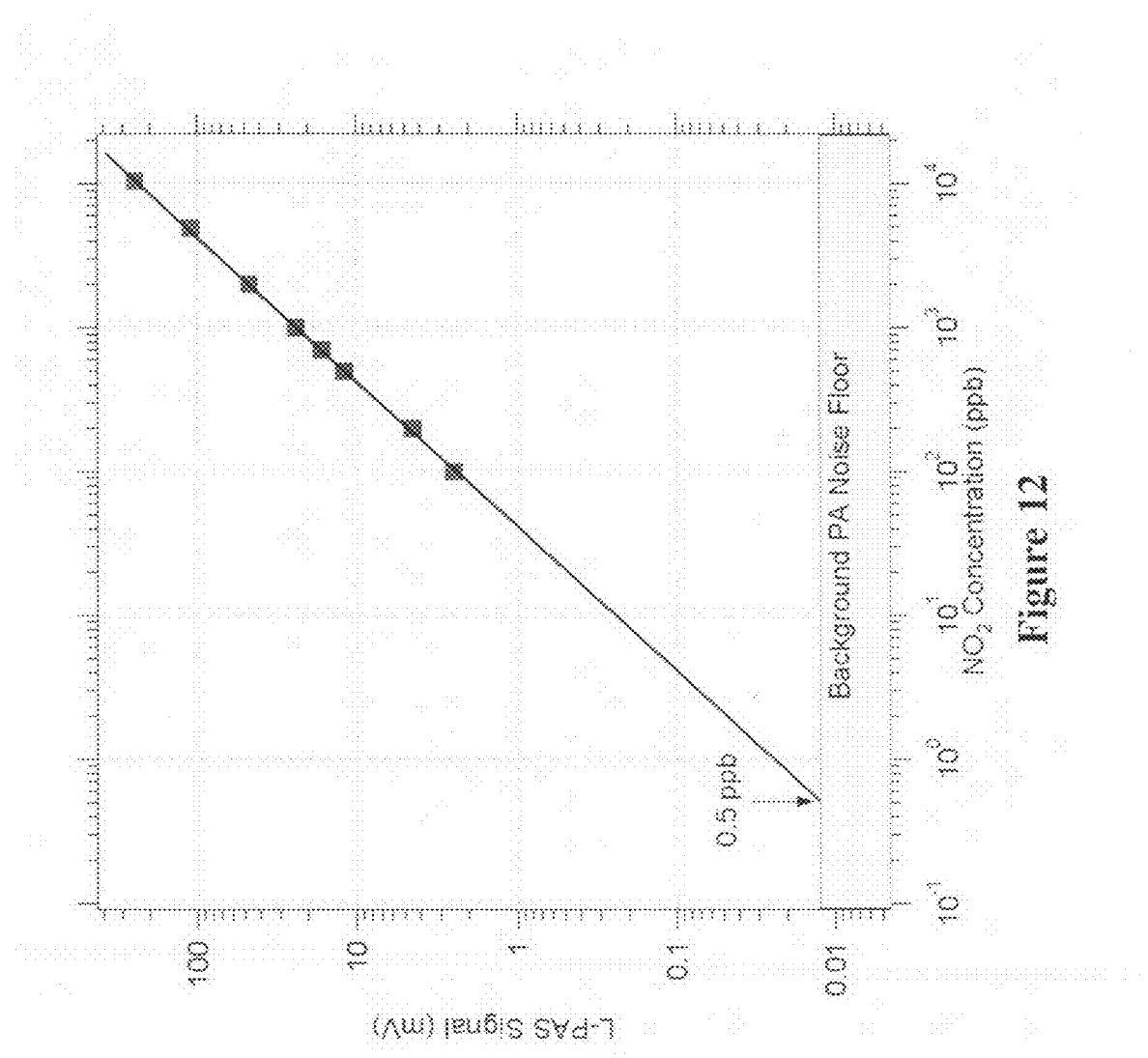
FIG. 12 is a diagram showing $NO_2$ L-PAS linearity. Unity signal to noise ratio corresponds to 0.5 ppb $NO_2$ detection limit (grayed-out area below 0.01 L-PAS Signal).

The 6,300 nm single wavelength tunable QCL was used for high resolution spectroscopy (FIG. 11) and sensitive detection (FIG. 12) of nitrogen dioxide, pollutant gas that results from industrial activities as well from automobile emissions. Data in FIG. 12 permits us to extrapolate the measurements to obtain a detectivity of 0.5 ppb for nitrogen dioxide using the broadly tunable external grating cavity QCL.

Sensitive Detection of Explosives

Reliability and reproducibility of the tuning of the single wavelength QCL permits us to use our QCL based laser photoacoustic spectroscopy system for the sensitive detection of home-made explosives such as triacetone triperoxide (TATP), its precursors, acetone and hydrogen peroxide, and conventional explosives such as trinitrotoluene (TNT).

Detection of TATP and Acetone

Triacetone triperoxide ($C_9H_{18}O_6$, molecular mass of 222.24 g/mol) is a powerful explosive that is easy to synthesize using commonly available household chemicals, acetone and hydrogen peroxide. Because of the simplicity of its synthesis, triacetone triperoxide (TATP) is often the explosive of choice for terrorists including suicide bombers. For providing safety to population, early detection of TATP and isolation of such individuals is essential. We report unambiguous, high sensitivity detection of TATP and its precursor, acetone, using room temperature quantum cascade laser photoacoustic spectroscopy (QCL-PAS). The available sensitivity is such that TATP, carried on a person (at a nominal body temperature of 37° C.), should be detectable at some distance. The combination of demonstrated detection of TATP and acetone should be ideal for screening at airports and other public places for providing increased public safety.

Unlike most other high explosives, TATP contains no nitrogen or nitrates. The absence of nitrates makes it difficult to detect using technologies that utilize nuclear quadrupole resonance for the detection of other explosives such as TNT, PETN, RDX, etc., all of which are nitrate rich. TATP is suspected as being the explosive that was used in London Underground bombings on Jul. 7, 2005 that killed more than 50 people and injured more than 700. Countless number of civilians have been killed by suicide bombers who often prefer TATP because of the relative simplicity of its synthesis. The notorious but unsuccessful shoe bomber in 2001 was suspected of carrying TATP. Finally, TATP can be readily synthesized from acetone and hydrogen peroxide. The present international air travel crisis owes much to the simplicity of synthesis of TATP and the absence of high sensitivity detection of TATP and its liquid precursors. Once the presence of TATP is established, its presence is easy to verify using a variety of wet chemical techniques. However, this adds nothing to public safety because the initial determination of the TATP is still missing. We demonstrate that this first crucial step, identification of the presence of TATP and its precursor, acetone, is now possible using quantum cascade laser based photoacoustic spectroscopy (QCL-PAS).

Because of the expected broad absorption feature of TATP, continuous tuning of the QCL wavelength is not necessary. Furthermore, use of a "Smart Grid" of wavelengths selected as described herein avoids measurements at the known wavelengths of the sharp absorption features corresponding to residual water vapor. We select the appropriate density of the grid, under computer control, depending on the nature of the target. For targets with narrow absorption features, such as acetylene, a dense grid has been used, while for targets with broad absorption features, such as TNT and TATP, a sparse grid can be used without any loss of spectral details.

Figure 13:
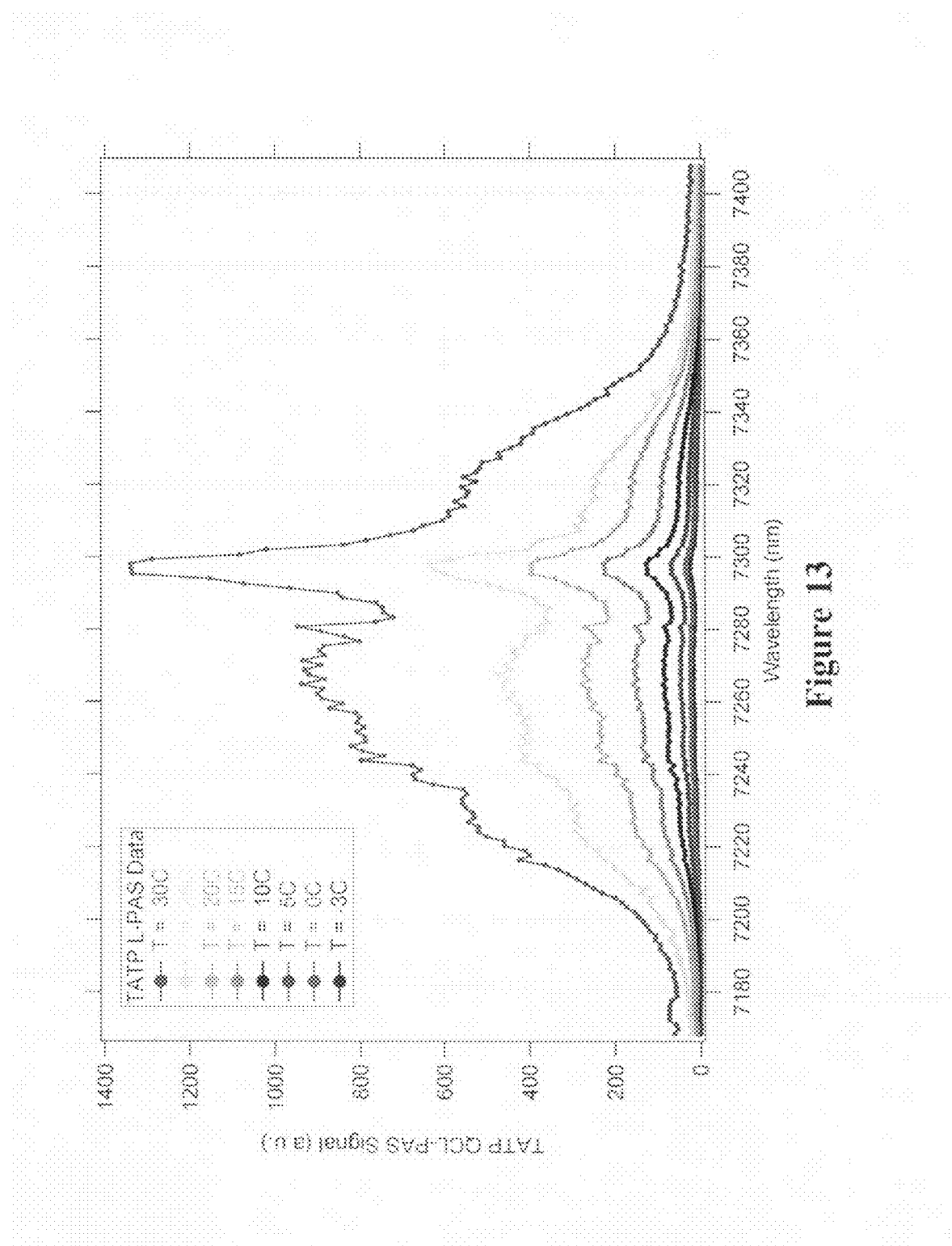
FIG. 13 is a diagram showing comparative laser photoacoustic signals measured from triacetone triperoxide (TATP) sample vapors at several temperatures.
Figure 14:
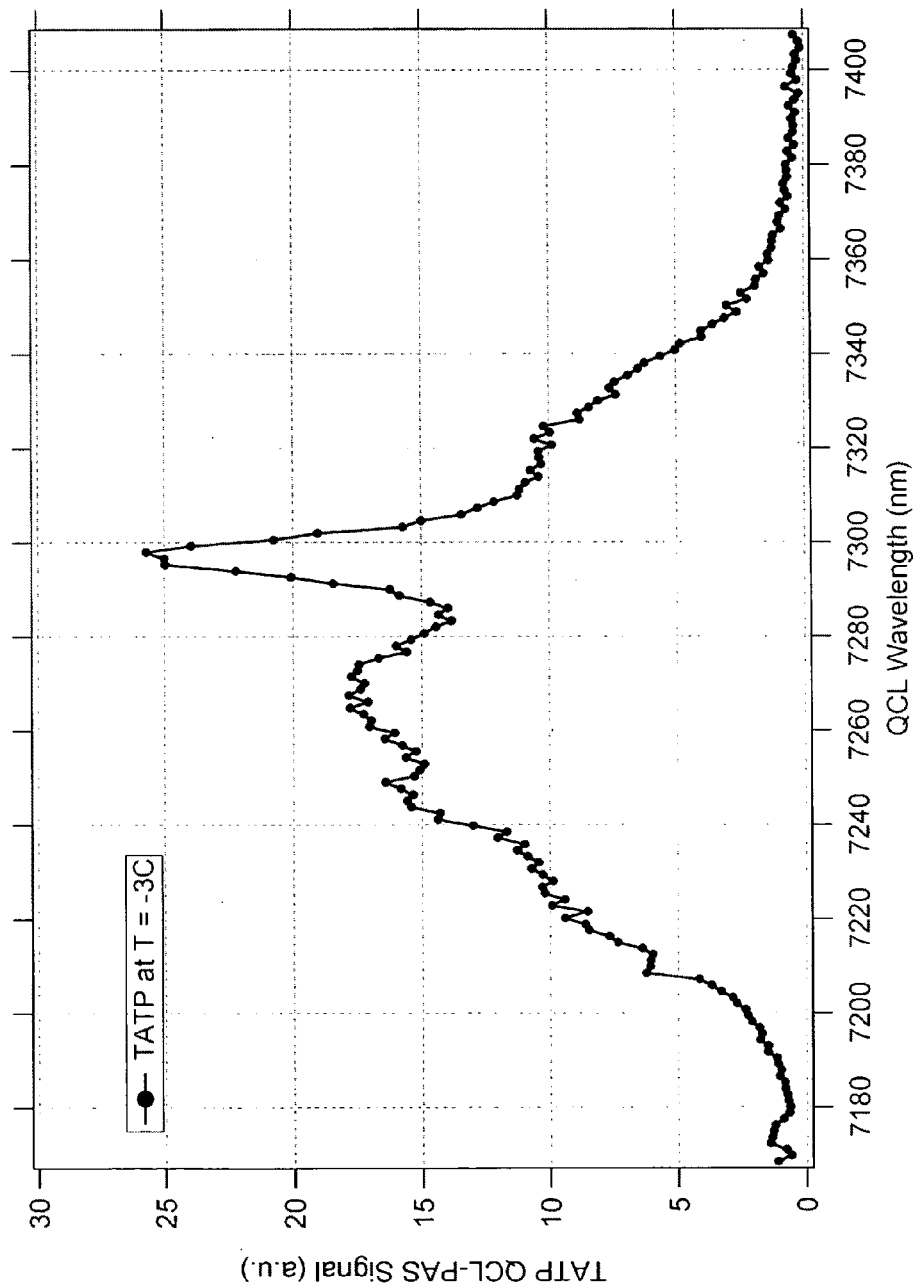
FIG. 14 is a diagram of a laser photoacoustic spectrum of TATP at −3° C.

FIG. 13 shows the measured QCL-PAS data for TATP at several different temperatures from 25° C. to −3° C. (the lower temperature limit is set by the presently used chiller). Very high signal-to-noise ratio spectra are obtained. To evaluate our detection sensitivity for identifying TATP, in FIG. 14 we show the lowest temperature (−3° C.) data on an expanded scale. A S/N ratio of in excess of 1000 is seen.

Figure 15:
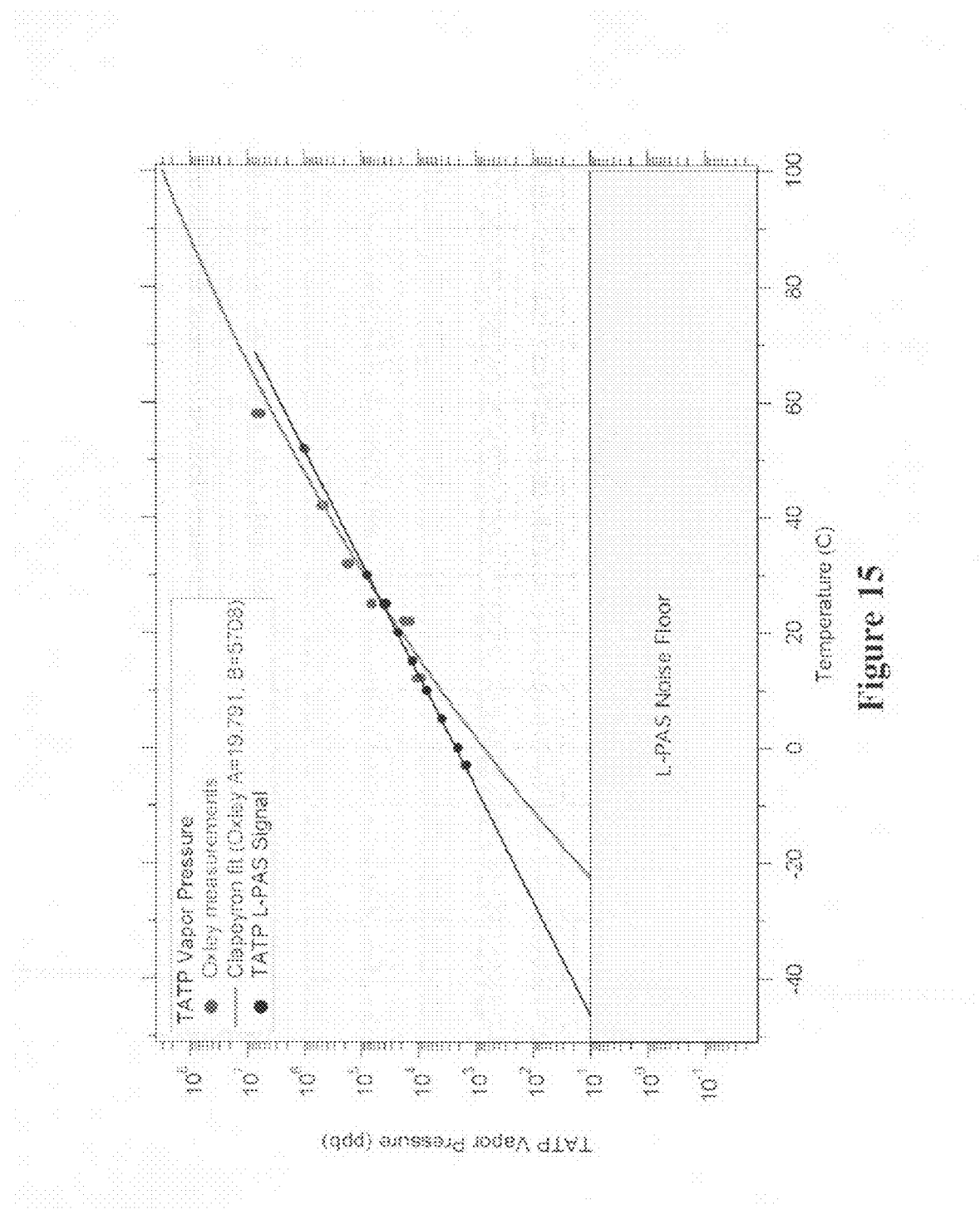
FIG. 15 is a diagram showing TATP L-PAS signal strength and TATP vapor pressure as a function of temperature along with a Clapeyron fit to the measured TATP vapor pressure (vapor pressure data from Oxley). The QCL-PAS data are fitted at T=25° C. point on the Clapeyron fit.

To convert the TATP temperature in to an equivalent vapor pressure, we use the data published by Oxley. FIG. 15 shows vapor pressure measurements of Oxley and a Clapeyron equation fit to the data as a function of temperature. We also show our QCL-PAS data over the temperature range that now extends below the lowest temperatures for which vapor pressure data are available. The QCL-PAS data are fitted to T=25° C. vapor pressure point on the Clapeyron fit. The QCL-PAS data fit the measured vapor pressure data of Oxley well in 12° C. to 30° C. region. However, at lower temperatures, where measured vapor pressure data are not available, the L-PAS data diverge form the Clapeyron fit. Since the L-PAS signal generation process is inherently linear at low concentrations of absorbers, we believe that the use of L-PAS data as a surrogate for vapor pressure measurements at low temperatures would improve the Clapeyron equation fit.

To estimate the ultimate TATP detection capability provided by QCL-PAS measurements, we show the L-PAS noise floor on FIG. 15. We estimate from the extrapolation of QCL-PAS data that TATP at vapor pressures as low as 10 ppb (which is approximately 10 picograms per cubic centimeter (~10 pg cm$^{-3}$)) should be possible with a S/N ~1. Incidentally, this extrapolation is independent of the Clapeyron fit. We cannot unequivocally convert the ~1 ppb sensitivity into a corresponding TATP temperature as yet.

Figure 16:
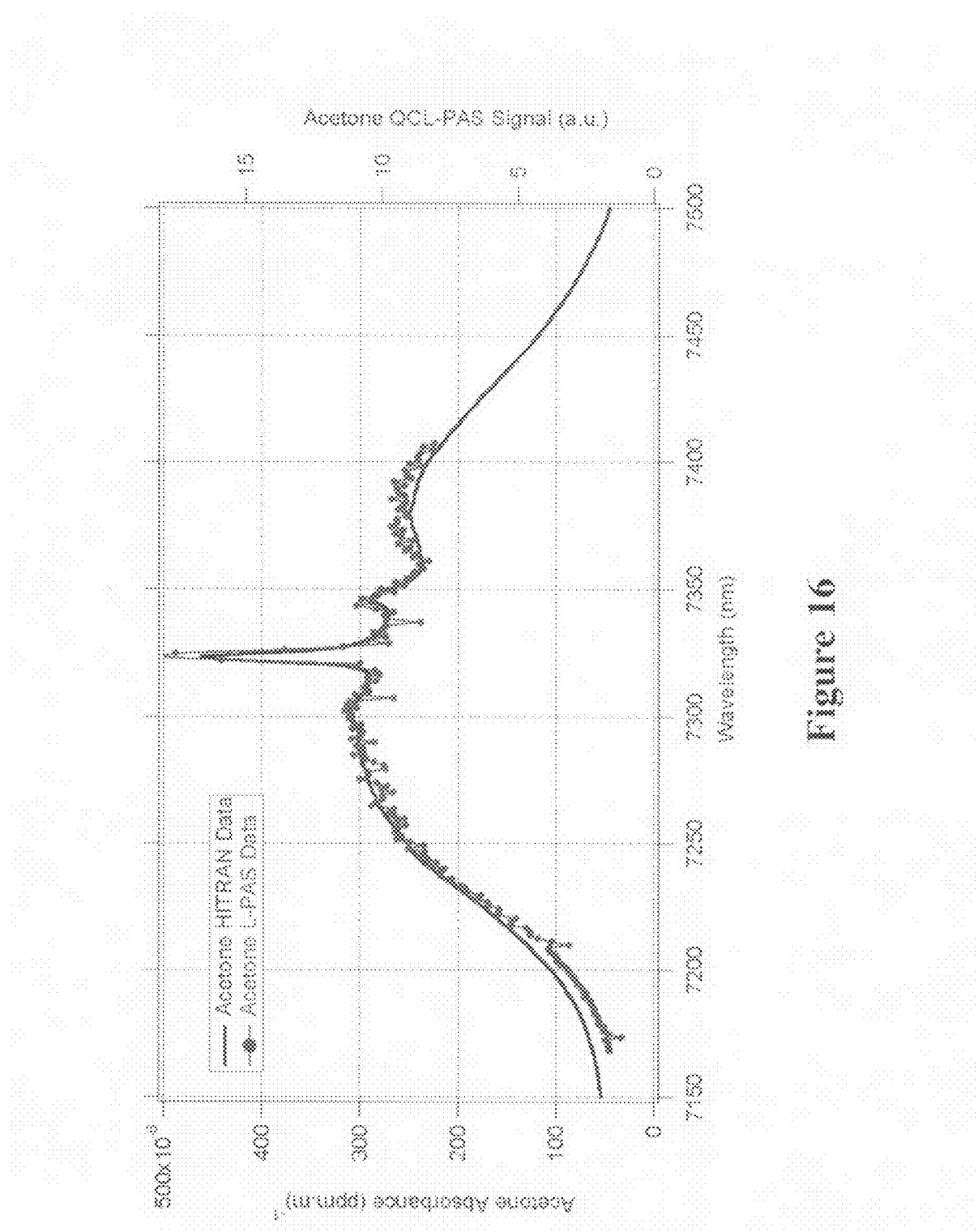
FIG. 16 is a diagram showing QCL-PAS signal for 1.4 ppm acetone (a precursor for synthesizing TATP) shown along HITRAN acetone absorption simulation.
Figure 17:
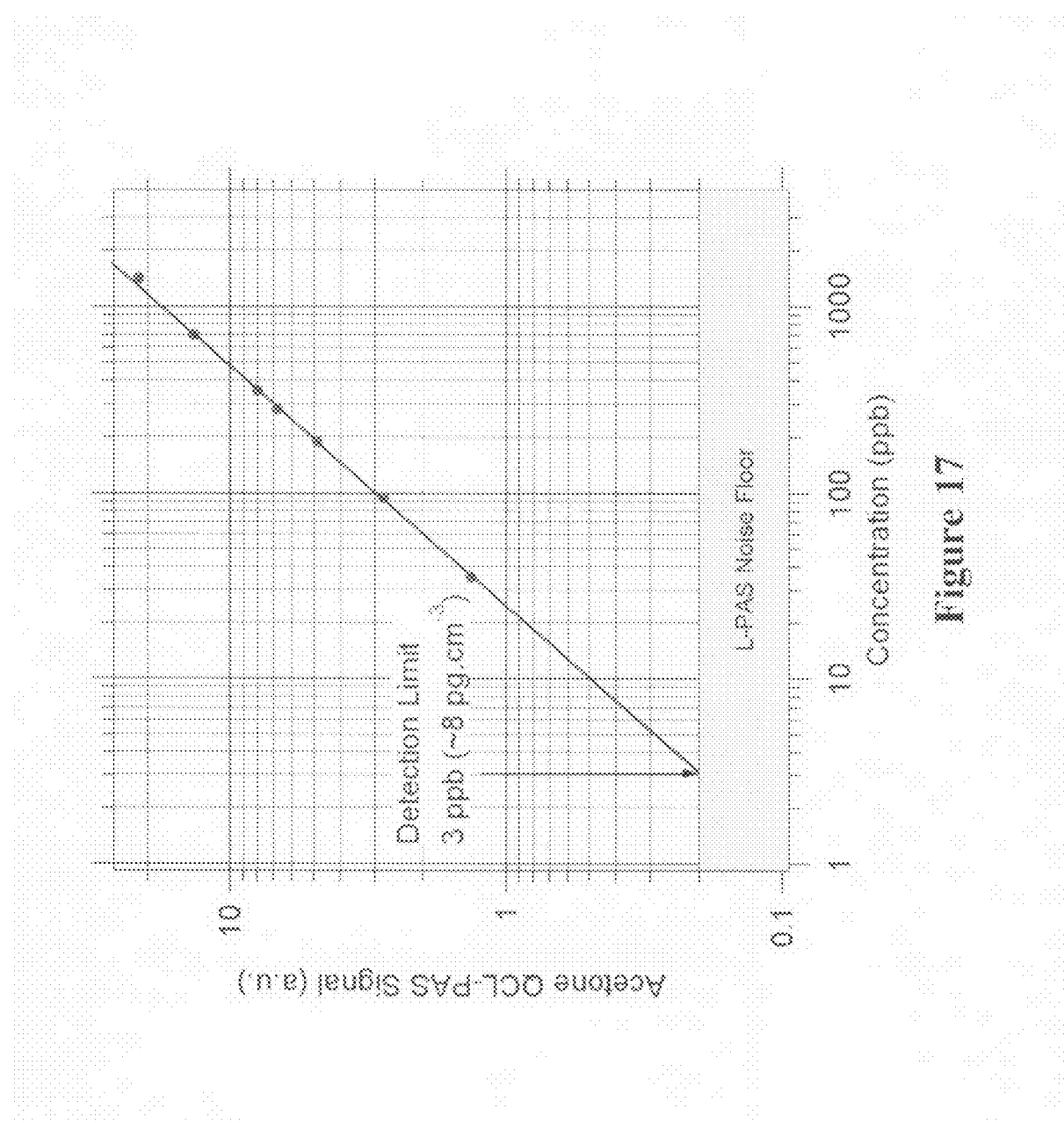
FIG. 17 is a diagram showing QCL-PAS signal for acetone as a function of acetone concentration with the L-PAS noise floor shown below 2 a.u. on the y-axis.

From the current interest in assuring safety of air travel it is clear that we need to detect not only TATP with very high sensitivity but also detect at least one of the precursors necessary to synthesize the explosive. FIG. 16 shows a QCL-PAS spectrum of 1.4 ppm acetone, one of the two principal ingredients for synthesizing TATP. Very high signal/noise ratio spectrum is seen. HITRAN simulation of acetone is also shown on the same figure and indicates excellent agreement between QCL-PAS measurements and simulated data. FIG. 17 shows acetone L-PAS signal versus acetone concentration along with the L-PAS noise floor. We can estimate that the lowest concentration that can be detected is about 3 ppb (~8 pg cm$^{-3}$) in the present preliminary studies. The acetone detection sensitivity value is comparable to the acetylene detection sensitivity value (2.5 ppb) reported earlier and is consistent with the relative absorption strengths of the two gases as reported in the HITRAN compilation. It should be noted that the accepted value of odor threshold for acetone is about 13 ppm although very wide variation in the number exists in the literature.

Detection of a Conventional Explosive, TNT

Detection of illegally transported explosives has become important since the global rise in terrorism subsequent to the events of Sep. 11, 2001. While not a choice of suicide bombers, TNT is considered a potent explosive for which techniques for detection on a person's body or in one's baggage is considered important for assuring safety of airports and air travel. As with detection of other similar compounds, such as chemical warfare agents, any detection scheme that claims to detect these targets must exhibit acceptable receiver operational characteristic (ROC) that assures detection at very low levels without unacceptable level of false alarms. The molecular weight of TNT ($C_7H_5N_3O_6$) is almost exactly identical with the molecular weight of nitroglycerine ($C_3H_5N_3O_9$) even though the chemical compositions of the two molecules are very different (TNT: 227.131 Da vs. NG: 227.0872 Da). The nearly same molecular weights often lead to problems for unambiguous detection of TNT using techniques that rely on measuring the molecular mass of the species. On the other hand, the differences in the chemical structure between TNT and nitroglycerine leads to noticeably different infrared absorption signatures making it possible to distinguish between the two. Moreover, the detection of TNT in vapor phase is made difficult by its low vapor pressure of approximately $2\times10^{-4}$ torr at 25° C. Nonetheless, the high sensitivity afforded by L-PAS shows that the vapor phase detection of TNT at an ambient temperature of approximately or roughly 25° C. is possible.

The 7300 nm QCL-PAS system spans a wavelength region from 7150 to 7500 nm and also covers the absorption spectrum of TNT (in addition to those of TATP and acetone described above). For exploring detection of TNT we provided a continuous flow of clean dry air over a sample of TNT and the emerging gas was continuously analyze by QCL photoacoustic spectrometer. The temperature of the TNT sample could be controlled from room temperature to 60° C. The gas transport lines from the TNT sample chamber to the photoacoustic cell and the photoacoustic cell were maintained at 60° C. to prevent condensation of TNT vapors either in the transfer lines on in the photoacoustic cell. The upper temperature limit was set by the photoacoustic cell microphone whose sensitivity begins to degrade significantly above 60° C. but is not a limitation for future operation of the cell at higher temperatures by using appropriate high temperature microphones.

Figure 18:
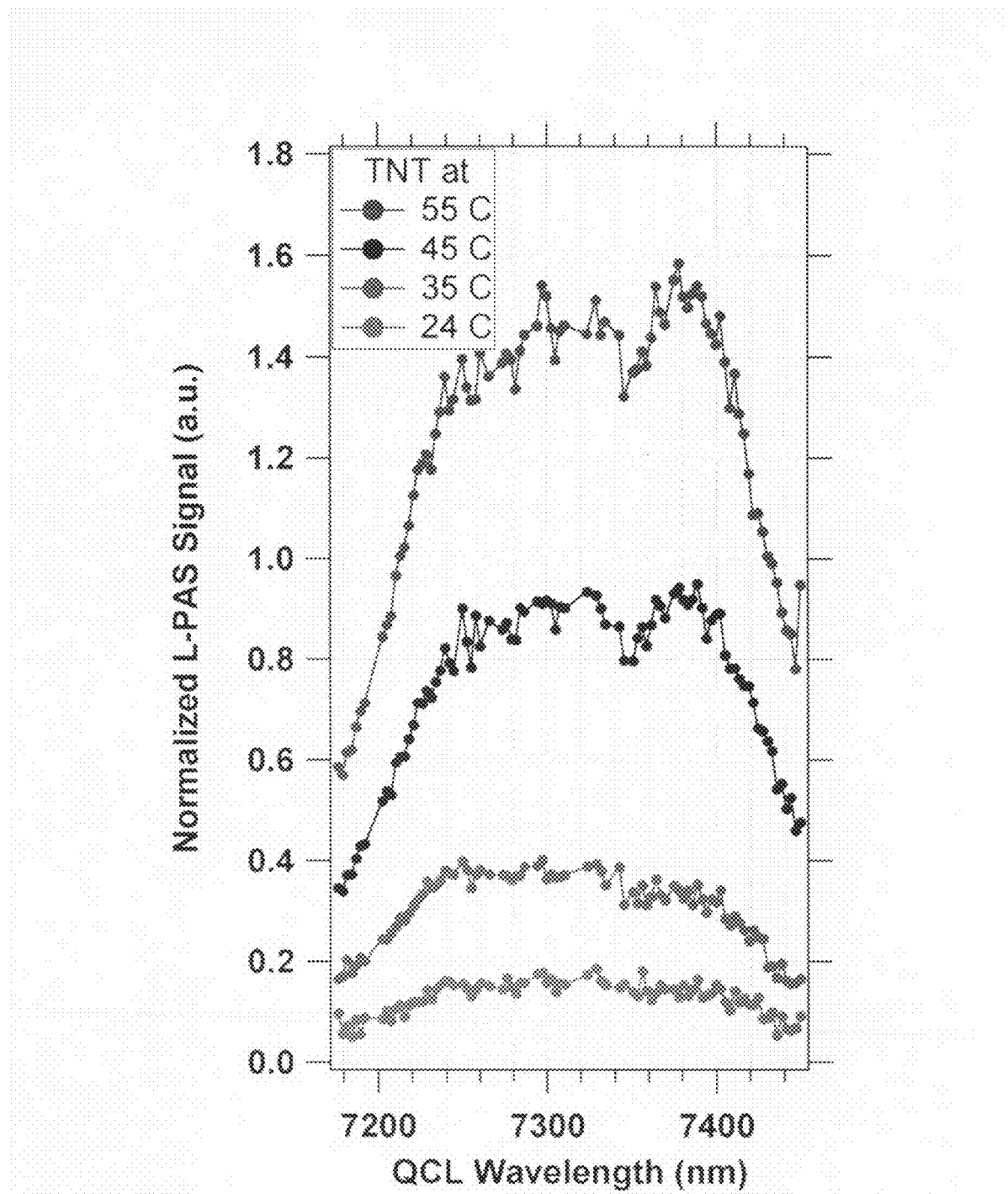
FIG. 18 is a diagram comparatively showing measured QCL-PAS absorption spectra of TNT at four different temperatures.

FIG. 18 shows an L-PAS spectrum obtained when the TNT sample was kept at 24° C., 35° C., 45° C. and 55° C. respectively. Note should be taken of three specific aspects of the PA (photoacoustic) spectrum. The first is that a number of sharp absorption features arising from residual water vapor in the system (as verified using water vapor absorption spectra obtained from HITRAN simulations) occur at certain wavelengths in the same region of wavelengths. These were avoided by using a smart grid of laser wavelengths that skips these specific wavelengths as the computer provides the tuning instructions to the EGC QCL.

The second is that the QCL-PAS spectrum is significantly broader than that would be expected. In fact, the QCL-PAS spectrum consists of two distinct features, one centered at ~7380 nm that matches the expected absorption feature of TNT and the second centered at ~7300 nm that arises from the yet unknown impurity in the commercial grade TNT. The unknown impurity was seen to be located on the surface of the TNT sample and the 7300 nm feature gradually disappeared as the TNT sample was kept at 100° C. for 48 hours while flushing the sample with clean dry air.

Figure 19:
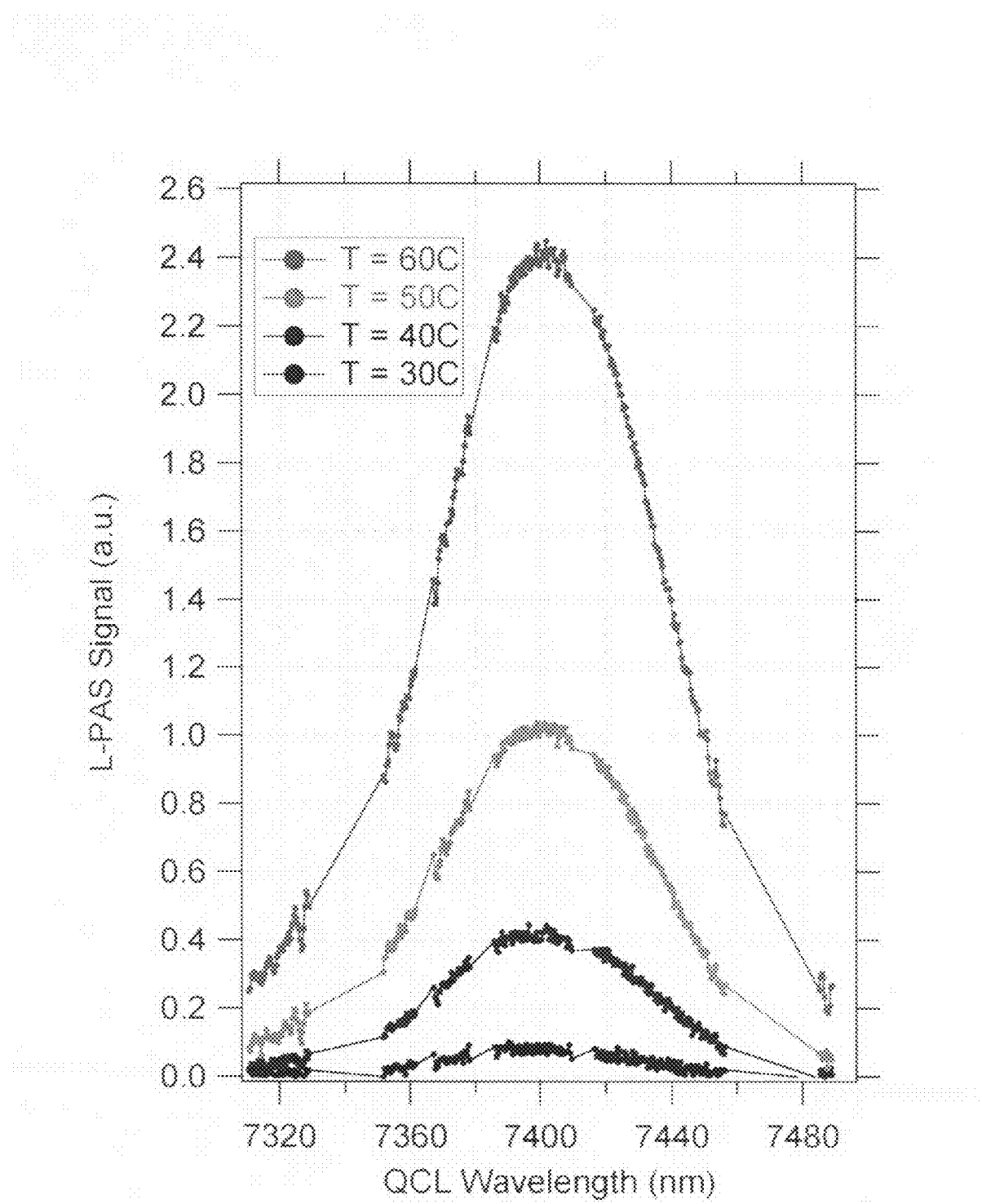
FIG. 19 is a diagram of a QCL-PAS spectrum of "cleaned up" TNT sample at three different temperatures using smart grid tuning algorithm.

FIG. 19 shows the measured L-PAS spectrum of "purified" sample of TNT vapor in a background of room air with relative humidity of about 40% at 25° C. The spectrum matches the expected position and width well. The spectra were taken using 300 discreet wavelengths determined by the computer using the smart grid algorithm that skips the wavelengths corresponding to the known strong absorption features of water vapor. We conjecture that the disappearing peak at 7300 nm could be used in the future to tag the origin and age of the TNT sample for forensic purposes. However, a confirmation of the conjecture will have to await getting samples of different age and origin from NAWS, China Lake. In either case, the shape and location information provides a powerful tool for QCL-PAS to uniquely identify TNT and minimize effects of interference.

Figure 20:
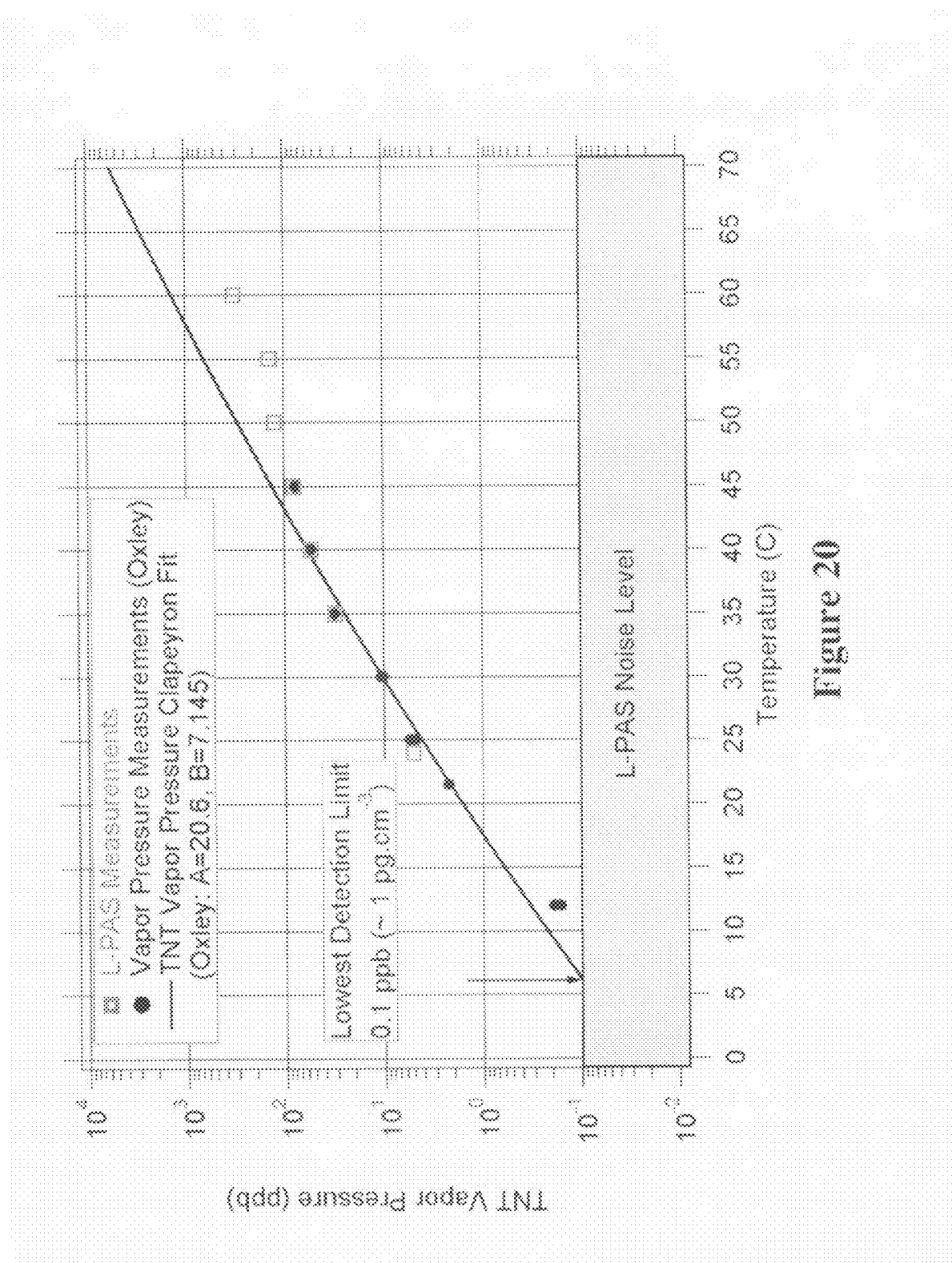
FIG. 20 is a diagram showing calculated vapor pressure of TNT (using Clapeyron fit) versus temperature and the measured photoacoustic signal strength at various temperatures.

The third aspect of the measured spectra (in FIGS. 18 and 19), which deserves mention, is that the signal feature in the ~7380 nm absorption region, grows rapidly as the TNT temperature is increased from 24° C. to 55° C. as would be expected form the temperature dependence of the vapor pressure of TNT shown in FIG. 20. We have plotted the measured QCL-PAS data for TNT on the same plot, anchoring the 50° C. QCL-PAS data on the vapor pressure vs. T plot. An acceptable correlation is seen between the vapor pressure data and the PA signal amplitude.

From the lowest temperature (24° C.) at which the photoacoustic spectrum is shown, we can estimate the detection sensitivity from known vapor pressure data for TNT. The vapor pressure of TNT is seen to be (from Clapeyron fit curve) about 3 ppb at 24° C. (~30 pg cm$^{-3}$). Comparing the L-PAS signal with the noise floor shown in the FIG. 20, we estimate that we can detect TNT at a level of 0.1 ppb (~1.01 pg cm$^{-3}$) with a S/N of 1 (i.e., TNT at temperatures as low as 5° C.). It should be noted, however, that the relationship of vapor pressure and temperature is dependent on the Clapeyron fit to the measured data.

QCL-PAS can Distinguish Between Various Explosives

Figure 21:
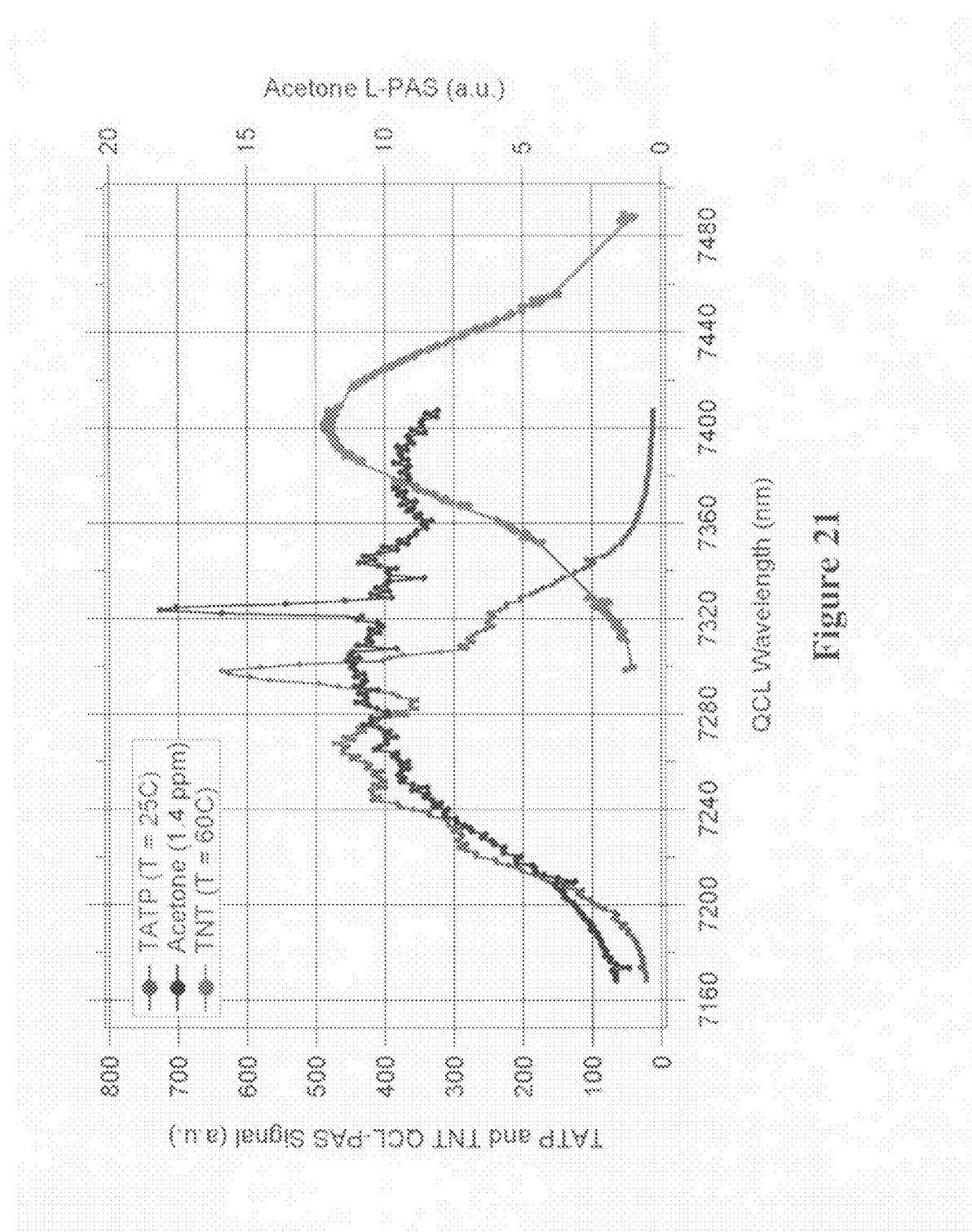
FIG. 21 is a diagram comparatively showing QCL-PAS absorption spectra of TATP (T=25° C., first peak left to right), acetone (1.4 ppm, second peak), and TNT (T=60° C., third peak).

The spectral features of TNT and TATP are so distinctly different that the system should be able to detect each of these three components unambiguously at very low concentrations (FIG. 21). Moreover, the use of an intelligent grid of discrete sampling wavelengths that avoids the strong, but sharp, absorption features of water vapor would be immediately deployable for real time screening of personnel and baggage at airports and other public places where threat from explosives and/or precursors is perceived. Such high sensitivity screening should lead to the relaxing of some of the draconian security measures that govern air travel today.

All-Mechanical Control of QCL Wavelength and Cavity Length

A method for mode-hop-free tuning of grating-coupled external cavity lasers may be based on a Littrow configuration in which the grating assembly moves along two perpendicular axis, resulting in simultaneous grating rotation and cavity length adjustment to track one longitudinal mode of the cavity. This improves laser power output despite the change in laser operating frequency that occurs with rotation of the grating. This configuration requires only one linear actuator and gives an exact solution of the problem of coordinating grating rotation with cavity length despite the presence of linear dispersion.

Electrically pumped semiconductor lasers are divided in two main categories: diode lasers based on inter-band transitions (between the conduction and the valence bands) and quantum cascade lasers based on intersubband transitions between confined states of the conduction band. Tunable external grating cavity diode lasers (EGCDLs) have been used for a long time in both laboratory and industrial applications including optical telecommunication equipment testing, optical metrology, and gas sensing. EGCDLs are attractive for the latter application because of their compactness, ease of use, and cost. However, to date most of the accessible spectral region has been in the visible and near-infrared (NIR) portions of the electromagnetic spectrum and has involved the use of diode lasers. This arrangement allows one to spectroscopically investigate only overtone and combination vibrational bands of most molecules. The fundamental bands, which have typically several orders of magnitude stronger absorption strengths, lie in the mid wavelength infrared (MWIR) and/or long wavelength infrared (LWIR) regions, between 3 and 12 µm.

The invention of the quantum cascade laser (QCL) in 1994 and its rapid development during the following decade led to room temperature continuous wave operation with power levels in excess of 100 mW between 3.8 and 9.6 µm. QCLs opened up a way to the realization of compact, ultra-sensitive, trace gas sensors based on absorption spectroscopy. Such trace gas sensors have a very wide field of applications including industrial process control, environmental air-quality monitoring, agricultural and industrial emission monitoring, chemical warfare agent (CWA) detection, and explosives detection. For the detection of heavy molecules with broad absorption features, detection of a target species in presence of interferences, or detection of several species simultaneously, external grating cavity QCLs (EGCQCLs) are preferred over the distributed feedback QCLs because of the broader tuning range that is accessible with a single EGCQCL.

To obtain mode-hop-free tuning of external grating cavity lasers, one needs to vary the cavity optical length while rotating the diffraction grating in order to preserve the coincidence between the grating-selected wavelength and a single longitudinal mode of the overall cavity. Without such coordination, mode-hopping between adjacent or available laser modes can occur on a generally unpredictable basis. Such coordination between grating angle and cavity length can be done straightforwardly by having separate actuators for controlling grating angle and cavity length, at the price of increased complexity and cost of the system. The optical length can also be adjusted by varying the injection current, the temperature, or both, in the case of semiconductor lasers. This method is intrinsically slow because the primary contribution to the optical length of the semiconductor laser comes from the injection current and/or the temperature dependence of the refractive index of the semiconductor laser material and one has to wait for the temperature of the active region to stabilize. This is especially true for QCLs in which the tuning mechanism is thermo-optic effect.

A more powerful approach is to design the mechanical arrangement in such a way that the cavity length and the grating angle are adjusted simultaneously to track one longitudinal mode by means of a single actuator. This problem, as applied to dye lasers, has been investigated in the eighties. McNicholl and Metcalf have given solutions based on rotation of the grating around a carefully chosen pivot point for the Littrow grazing incidence with a tuning mirror (Littmann-Metcalf), and grazing incidence with Littrow grating configurations. These methods have been successfully applied to EGCDLs by several authors.

We have discovered a different method in which the grating moves along two perpendicular planes and is seen to be especially suited for making EGCQCLs.

Figure 22:
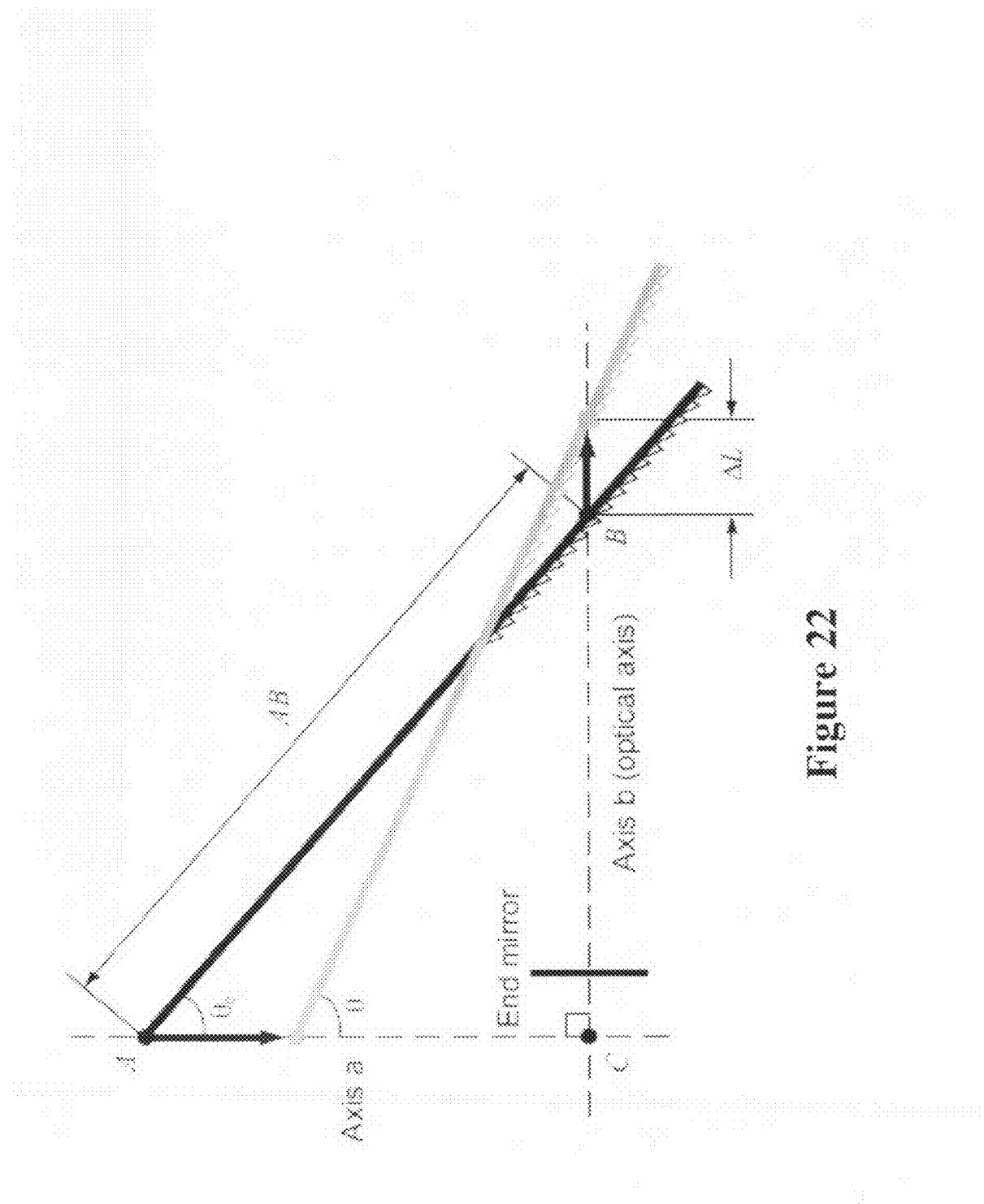

The example set forth herein uses a system having a laser consisting of gain element, a collimating lens, and possibly other elements in which the wavelength selection process is achieved by means of a diffraction grating in Littrow configuration (FIG. 22). We assume that the gain element is anti-reflection coated so that we can neglect the coupled cavity effects. In this case, the lasing mode is determined by the grating angle and the overall cavity length only.

The grating feedback into the gain element is different from zero only for a narrow wavelength region centered around $$\lambda_G(\theta)=(2d/k)\sin\theta \tag{5}$$

where d is the grating period, k the diffraction order that is used, and θ the angle between the normal to the grating and the optical axis. The cavity modes are given by the condition that the number of half-wavelengths in the cavity is an integer: $L=m\lambda_m/2$, where L is the optical length of the cavity and m is an integer. Let $L_0$ be the optical length of the cavity at the starting angle $\theta_0$. We assume that $\lambda_G(\theta_0)$ coincides with a longitudinal mode $\lambda_m=2L_0/m$. Experimentally this initial condition can be obtained by slightly adjusting the injection current or by small adjustment in the cavity length. In order to preserve the concurrence of the angle θ and the proper cavity length when the grating is rotated, the cavity length, L, should change by an amount $\Delta L(\theta)$:

$$\lambda_m(\theta)=2[L_0+\Delta L(\theta)]/m \tag{6}$$

In cases where the movement of the grating includes a translation along its own plane, as in the case for the pivot point methods, it is necessary to take into account the dephasing that this translation induces in the equation for $\lambda_m(\theta)$. But since this effect is not present in our method, we omitted the corresponding term in equation (6).

The required angular and linear movement of the grating may be achieved by means of a mechanical assembly of which a point B moves along the optical axis b and another point A moves along an axis a perpendicular to optical axis b and to the grating lines (FIG. 22). This configuration produces a cavity length variation of the form $$\Delta L(\theta)=AB(\sin\theta\sin\theta_0) \tag{7}$$

Inserting in equation (2) and requiring that $\lambda_m(\theta)=\lambda_G(\theta)$, one gets AB=md/k and $L_0$=ABsin$\theta_0$. These relations are equivalent. One can be obtained from the other using the initial condition $\lambda_m(\theta)=\lambda_G(\theta_0)$. Adding $\Delta L$ on both sides of the second relation, one gets $$L(\theta)=AB \sin \theta \tag{8}$$

The geometrical interpretation is straightforward: the projection of the segment AB on the optical axis has to be equal to the optical length of the cavity.

Figure 23:
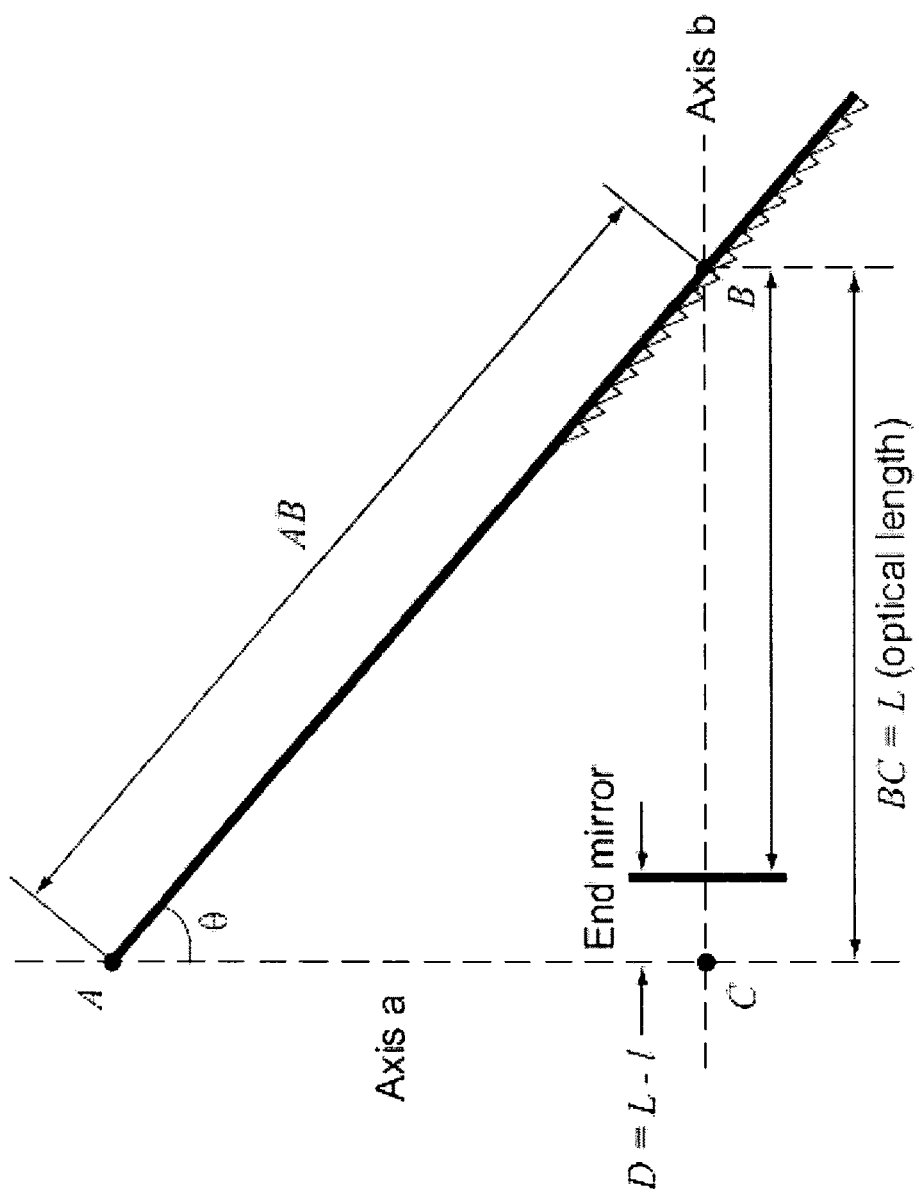
FIG. 23 shows a schematic cross section of the required cavity setting for mode-hop free tuning. The projection of the segment AB on the optical axis has to be equal to the optical length of the cavity L.

This allows us to determine the position of the back mirror with respect to the axis a. The distance D between these two has to be equal to the difference between the optical length L and the physical length I of the cavity (see FIG. 23):

$$D = L - l = \Sigma_i(n_i-1)l_i \tag{9}$$

where the index i runs over the optical elements inside the cavity, $n_i$ and $l_i$ being the refractive index and length of element i, respectively. The difference in the optical length and the physical length arises from the finite refractive index of the gain element inside the cavity (not shown). In the specific case where there are no other sources that change the propagation properties of the electromagnetic wave, i.e., dispersion, the problem of concurrent change of cavity length, L and the grating angle θ has now a closed form solution.

Since semiconductor lasers generally contain a waveguide structure, they present modal refractive index dispersion. That is, their modal refractive index, and consequently their optical length, are not constant as functions of wavelength. To the first order, this variation can be approximated as linear. However, if neglected in the design of the system, this dispersion has strong detrimental consequences on the tuning method set forth herein which relies on varying the optical cavity length while rotating the grating in order to preserve coincidence between grating-selected wavelength and a longitudinal Fabry-Perot mode of the cavity. There are detectable effects arising from waveguide dispersion as well as dispersion in other optical elements of the cavity on tuning method disclosed herein.

Prior attempts to resolve this dispersion problem did not take this effect into account. One attempt resulted in an observed a mode-hop-free tuning range of ~1% of the center wavelength. An improved version included the possibility of rotating the translation axis a (see FIG. 22) to compensate for dispersion. This approach demonstrated a larger tuning range of more than 5% of the center wavelength.

Continuously tuning the laser in the presence of dispersion may be achieved by positioning the translation axis a at a different location. This novel solution provides an exact solution to the problem in the case of linear dispersion (where refractive index which depends linearly on the wavelength). By providing an exact solution to the problem, the mode-hop-free tuning range can be made arbitrarily broad if one can build a sufficiently precise mechanical setup.

In order to take into account linear dispersion in our cavity, we introduce a dependence of $L_0$ on $\lambda$:

$$L_0(\lambda)=L_0(\lambda_0)+b(\lambda-\lambda_0) \tag{10}$$

with $b=dL_0/d\lambda=\Sigma_i(dn_i/d\lambda)l_i$. The substitution of the expression (6) in (2) leads to:

$$\lambda_m(\theta)=2[L_0(\lambda_0)b\lambda_0+\Delta L(\theta)]/(m-2b) \tag{11}$$

Requiring $\lambda_m(\theta)=\lambda_G(\theta)$ as before, we get $AB=(m-2b)d/k$ and $L_0-b\lambda_0=AB\sin\theta_0$. Inserting the definitions of $L_0$ and b, the quantity $L_g=L_0(\lambda_0)-b\lambda_0$ can be written as $$L_g=\Sigma_i[n_i(\lambda_0)-\lambda_0 dn_i/d\lambda]l_i \tag{12}$$

One can recognize the expression of the group refractive index $n_g=n(\lambda)-\lambda dn/d\lambda$. The result of preceding paragraph obtained in (9) has thus to be modified in presence of dispersion as follows:

$$D=L_g-l=\Sigma_i(n_{g,i}-1)l_i \tag{13}$$

D has to be equal to the difference between the group optical length and the physical length of the cavity. It should be noted that this method still gives an exact solution of the problem in this case.

For mode-hop free tuning range in case of non-ideal positioning, let us suppose that the distance between the axis a and the back mirror deviates from the ideal distance, given by equation (13), by a small amount $\Delta D$, i.e., that the cavity length is equal to $L(\theta)=\Delta D+AB\sin\theta$. In this case, the number of half wavelengths (μ) selected in the cavity by the grating, $$\mu=2L(\theta)/\lambda_G(\theta) \tag{14}$$

is no longer constant. The lasing mode is the Fabry-Perot mode $\lambda_m$ whose wavelength is the closest to $\lambda_G$, that is the one for which m=integer(μ). The mode-hop free tuning range is given by the condition that the variation of μ has to be smaller than one (1). Introducing the expressions for $L(\theta)$ and $\lambda_G(\theta)$ in equation (10), one gets:

$$\Delta\mu=2\Delta D[1/\lambda_{min}-1/\lambda_{max}]1 \tag{15}$$

In this last equation, we have assumed that the tuning range is much larger that the free spectral range of the cavity and have also chosen the lasing wavelength by $\lambda_G$ at its extremities where the above requirement no longer holds.

This equation gives the mode-hop free tuning range (in wavenumbers) as a function of the departure $\Delta D$:

$$\Delta\nu=\lambda_{min}^{-1}-\lambda_{max}^{-1}=1/2\Delta D \tag{16}$$

Figure 24:
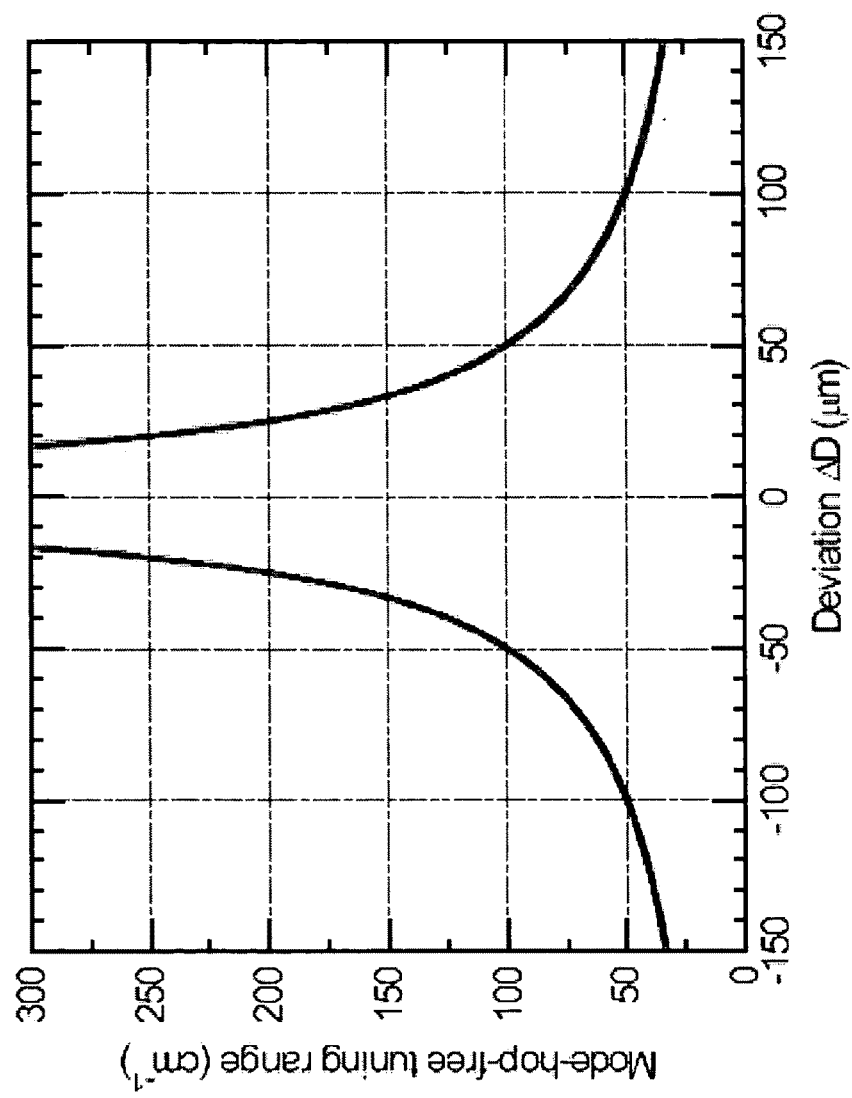
FIG. 24 is a graph showing mode hop free tuning range as a function of the departure of distance D from its ideal value, deviation ΔD (μm) spanning from −150 to 150.
Figure 25:
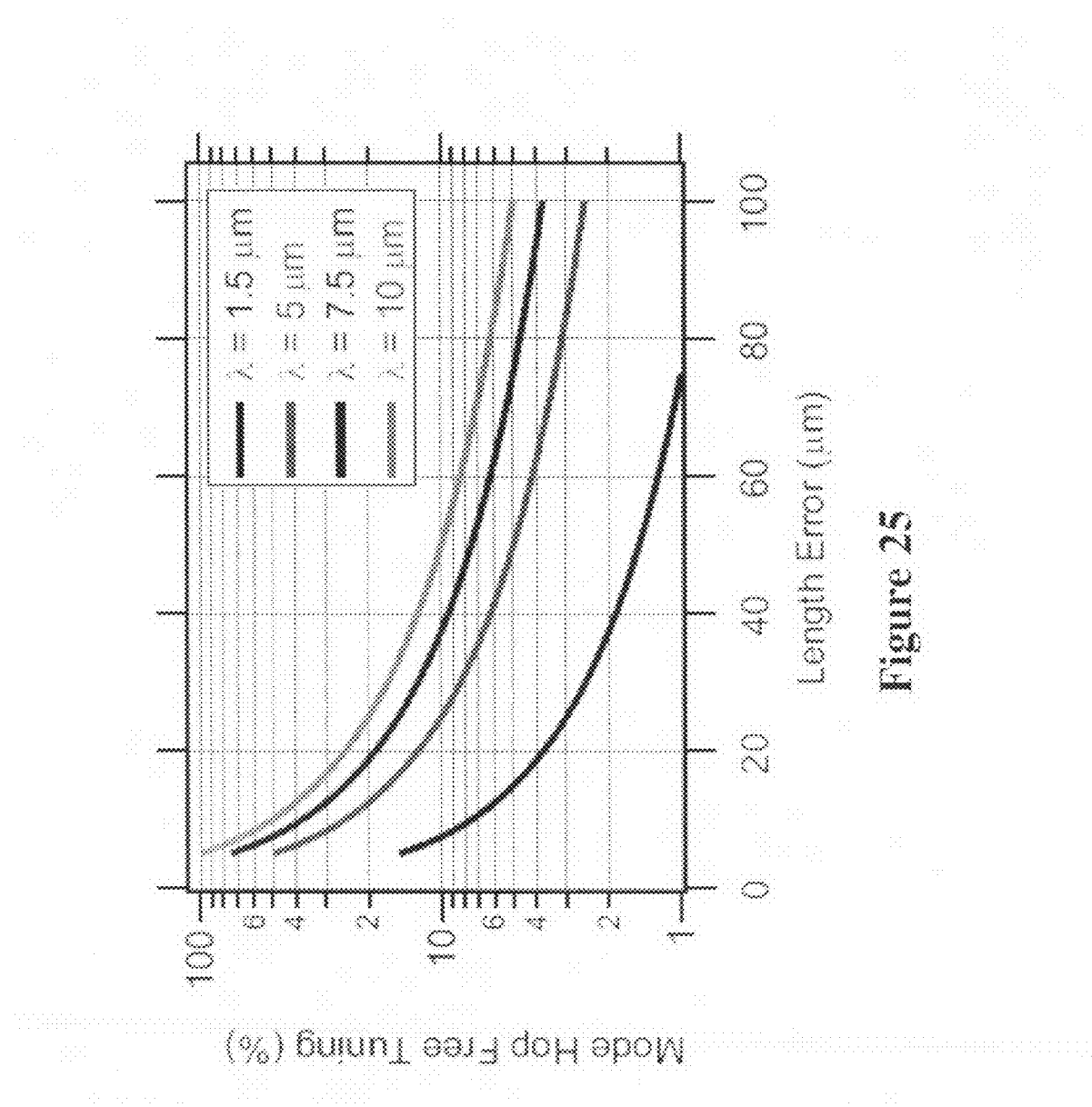
FIG. 25 shows in graphic form mode hop free tuning range in percent of the center wavelength as a function of the departure of distance D from its ideal value. The y-axis of the graph spans from 0 to 100 logarithmically

This result is represented graphically in FIG. 24. It is interesting to note that a tuning range of one hundred wavenumbers requires only a tolerance of ±50 μm on the position of this axis a, i.e., in the distance D derived in equation (13).

Figure 26:
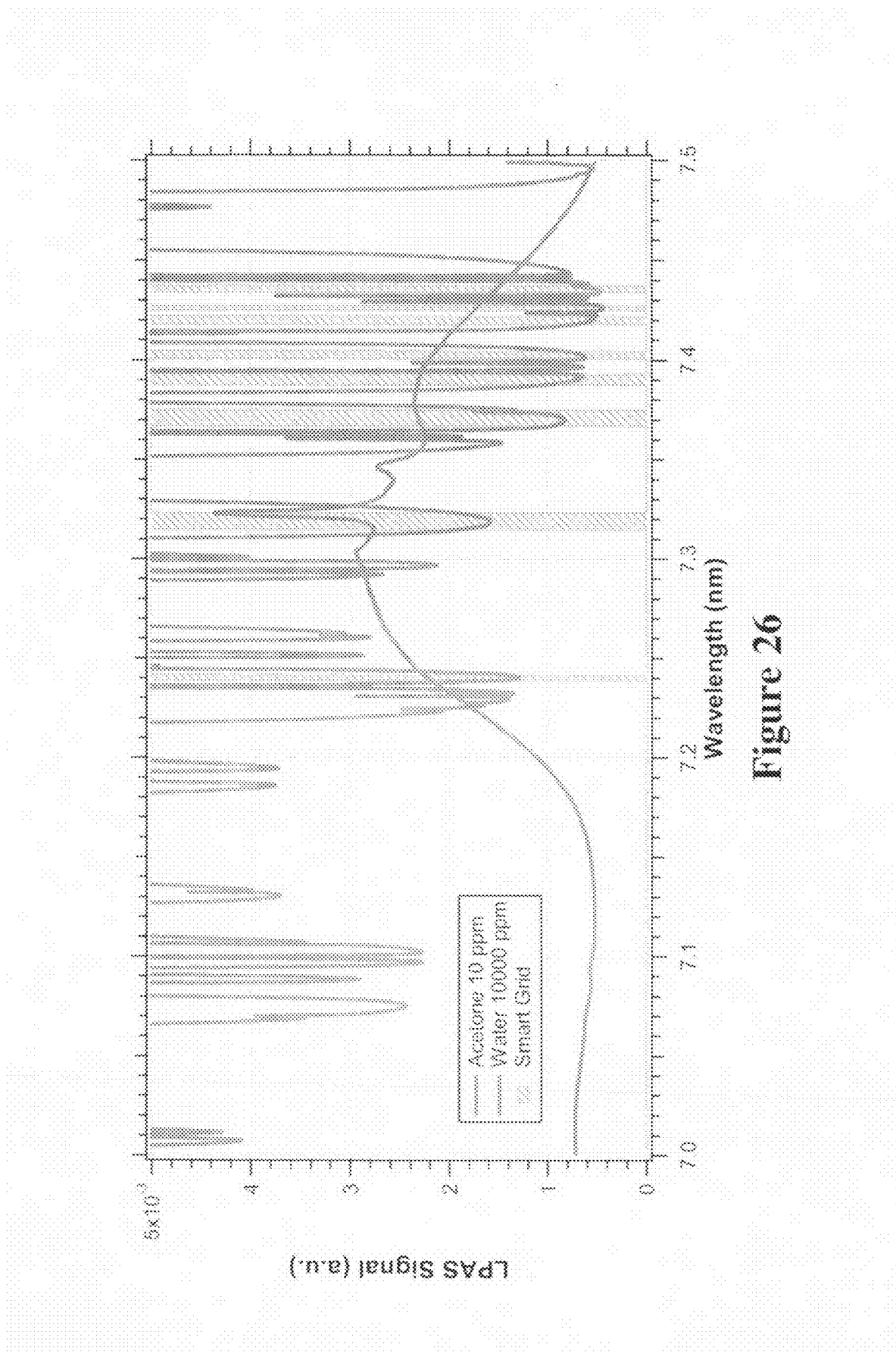
FIG. 26 is a diagram showing a simulation absorption spectrum of acetone (ascending 3-peak curve) and water (7-7.5 μm)

Written in an alternative form, equation (16) gives the relative tuning range as a function of the center wavelength λ:

$$\Delta\lambda/\lambda=\lambda/2\Delta D \tag{17}$$

which shows how mode-hop-free tuning is simplified when working at longer wavelengths. The fundamental reason behind this is that, in order to avoid a mode hop, the cavity length has to be controlled to a precision of ±λ/4. FIG. 26 portrays graphically the tuning range in percent of the center wavelength obtained for three typical QCL wavelengths of 5 μm, 7.5 μm and 10 μm, and a telecom diode laser wavelength of 1.5 μm, for cavity length deviation up to 0.1 mm.

In conclusion, a new method for continuous tuning of external cavity lasers has been achieved which is fundamentally different from the prior pivot point methods. It provides an exact solution of the coordination problem even in the presence of linear dispersion.

This novel method is particularly attractive for quantum cascade lasers (QCLs) because the mechanical tolerances are somewhat relaxed for mid wave infrared and long wave infrared wavelengths. In addition, the scheme permits one to get around the current tuning that is required at present that has proven to be slow because of the large temperature changes required.

The method presented herein is in principle applicable to any kind of external grating cavity laser, but since the size of the grating assembly grows linearly with the gain medium length, it is particularly well suited to semiconductor lasers in which the high gain occurs with chips only a few millimeter long.

Smart Grid Algorithm

The Smart Grid laser tuning algorithm for detection of a target species tunes the laser across different wavelengths of the target species absorption signature, but skips the wavelength regions in the frequency spectrum where potential interferences have large absorption features and are expected in high concentrations. This provides for better interference rejection as well as improving measurement time.

Gas detection using photoacoustic spectroscopy involves tuning a laser across different wavelengths and recording the acoustic transducer signal from the cell. When this signal is recorded across different wavelengths, it produces a unique signature for each molecule. In the real world, gas samples are composed of many different molecules (a "soup"). When the signature of the soup is linearly deconvolved against a standardized library of the target species and a list of expected interferents, it produces a concentration reading for the target gas as well as for the interferences. L-PAS is very useful for sub-ppb (parts per billion) detection of gas species.

To guarantee high sensitivity measurements in L-PAS, it is important to consider what wavelengths a laser can tune to obtain a good photoacoustic signature of the target species. Equally important is identifying potential interferents in the working region, and looking at the absorbances of the interferents at their expected concentrations. In the case that the interferents have very large absorbances which could potentially drown the signature of low concentrations of the target species which we wish to detect in a blanket of noise riding on top of the absorption signature of the soup, we simply choose to skip this region. Beginning with the complete laser tuning region where the target has large absorption, we eliminate all the regions where expected interferents have large absorption. This elimination is a key step in obtaining a rapid and sensitive L-PAS measurement. Once all the undesirable regions have been eliminated from the complete working region of the laser, we call the left over regions a "smart grid" for L-PAS.

The procedure for the "smart grid" algorithm includes the following steps:
1) Identify and select regions in the frequency range of the laser which meets all the following criteria:
   a) Target species has large absorption;
   b) expected interferents have low absorption at their expected concentrations; and
   c) Signature of target is linearly independent of signature of interferents.
2) These regions combined are now called the "smart grid."
3) Perform a scan across the smart grid and collect photoacoustic data.
4) Linearly deconvolve photoacoustic data against a standardized library of the target species and list of expected interferents, and obtain a gas concentration measurement.

To demonstrate the improvements in PFA (probability of false alarms) and measurement time (throughput) of the smart grid algorithm we chose to detect acetone in the presence of water as an interferent in the 7.0 to 7.5 µm region. 1000 scans were performed using the full available range (7.0-7.5 µm), and then another 1000 scans were performed using a smart grid of frequency points, which we identified (see FIG. 26). We had about 1% noise riding on top of our signal.

Figure 27:
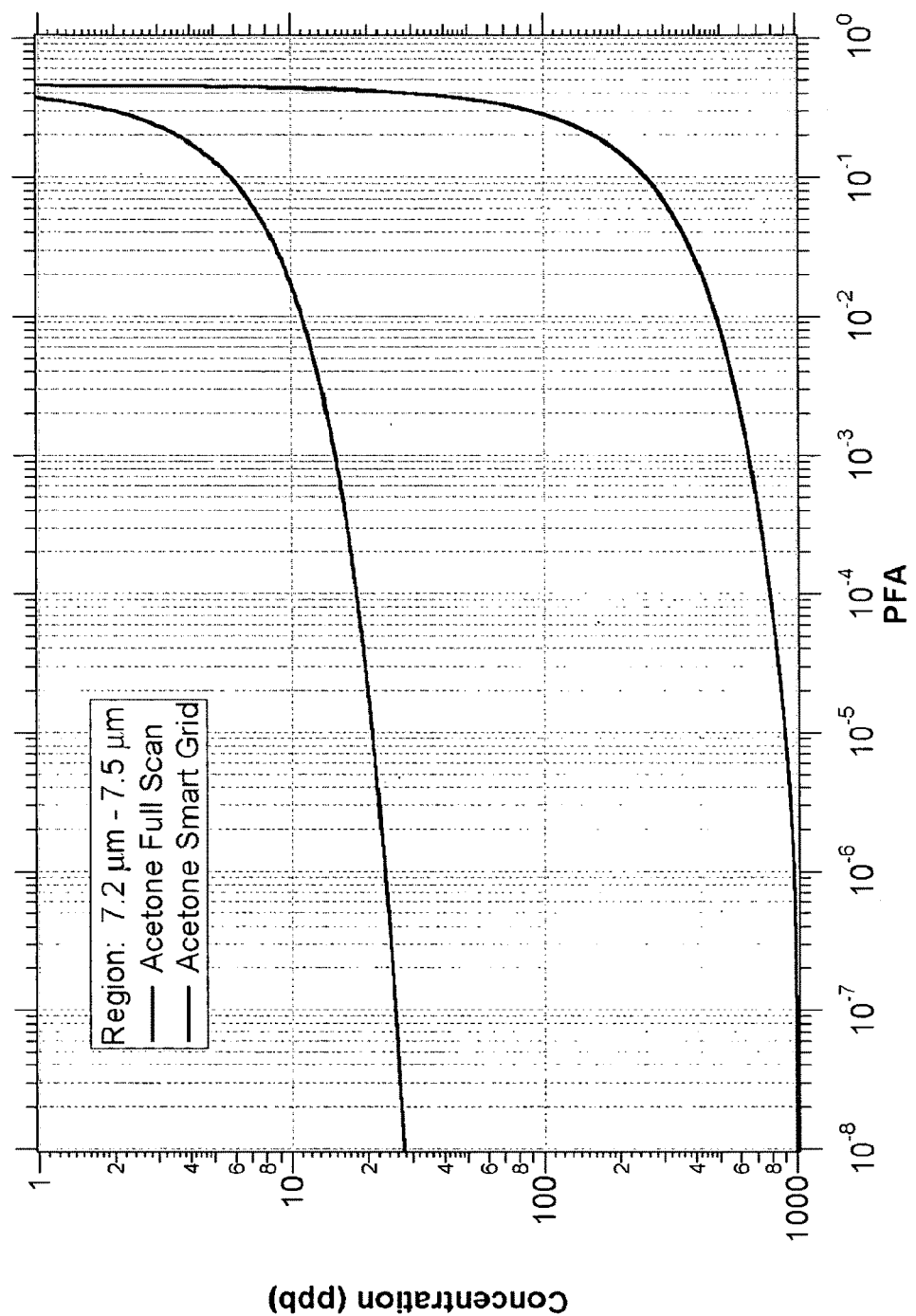
FIG. 27 is a diagram showing PFA for acetone in the presence of 10,000 ppm of water using the full scan (lower curve) and smart grid (upper curve) (7.2 mm-7.5 mm).

To characterize the detection limit in parts per billion (ppb) vs. Probability of False Alarms (PFA), we used 10,000 ppm of water and plotted ROC curves for acetone. The results were as expected and the smart grid showed improvement in the PFA by a factor of 30 for lower detection thresholds (see FIG. 27). The measurement time (throughput) also improved by a factor of 15 for smart grid detection.

Figure 28:
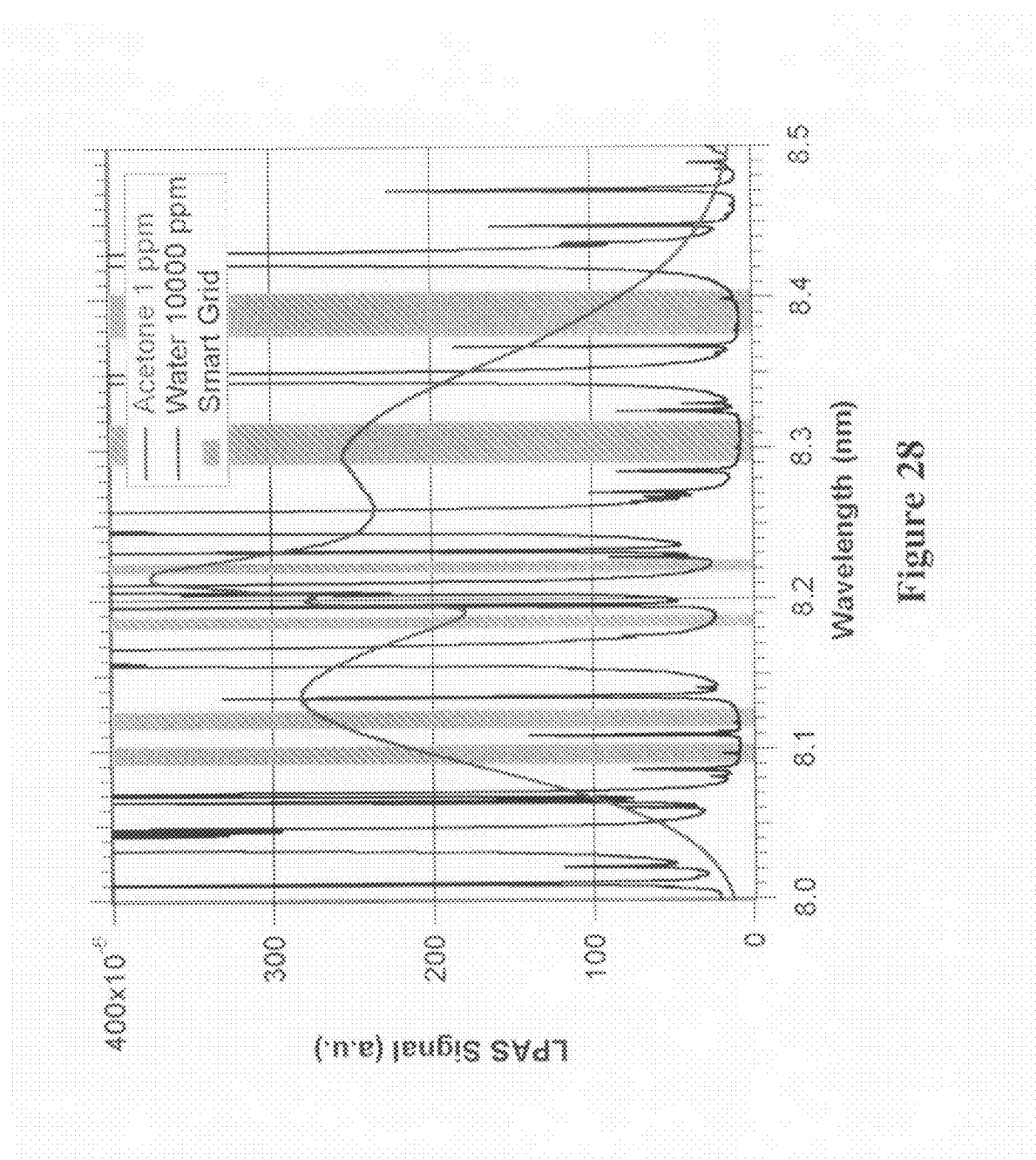
FIG. 28 is a diagram showing simulated absorption spectrum of acetone (ascending 3-peak curve) and water (descending multi-peak curve) (8.0 μm-8.5 μm).
Figure 29:
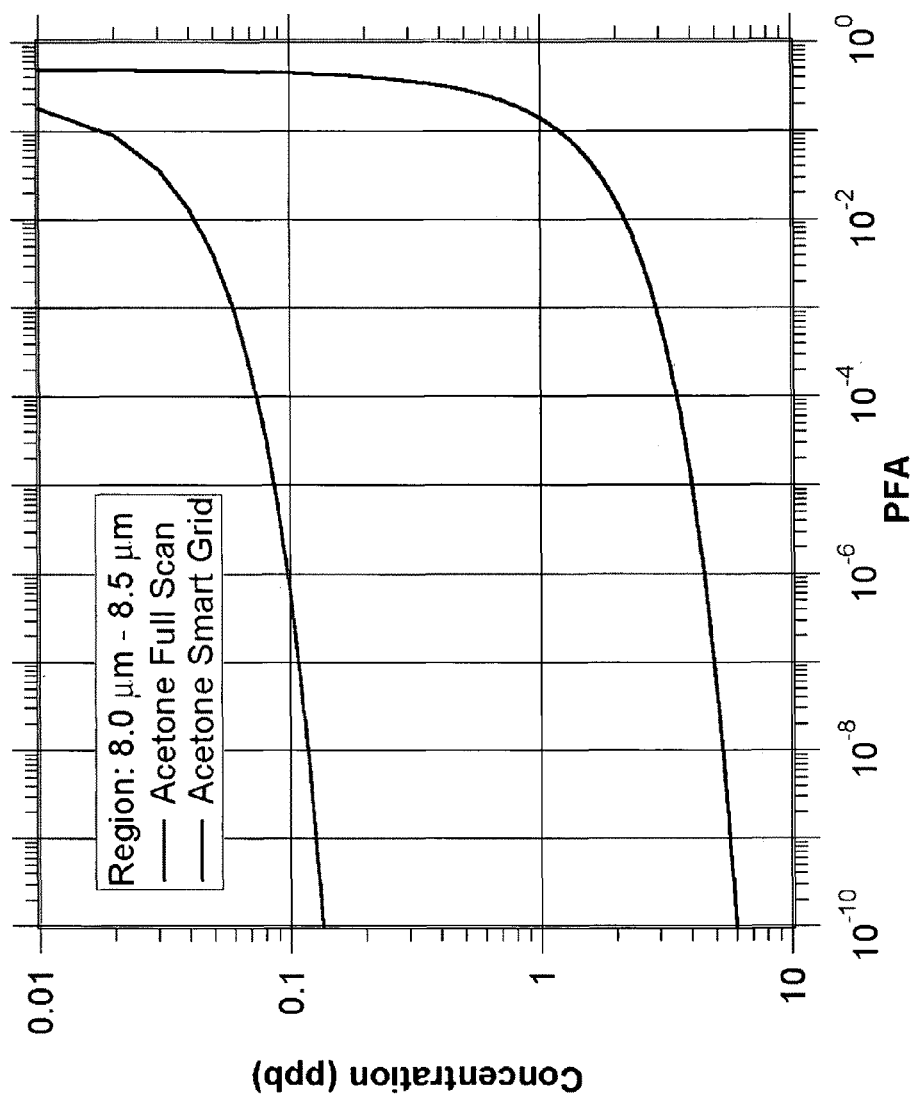
FIG. 29 is a diagram showing PFA for acetone in the presence of 10,000 ppm of water using the full scan (lower curve) and smart grid (upper curve) (8.0 μm-8.5 μm).

A similar simulation was carried out for the 8.0 to 8.5 µm region where water has a much lower absorption (FIG. 28) and the absorption features for acetone remained similar in shape and size. Here the smart grid showed improvement in the PFA by a factor of 40 for lower detection thresholds (see FIG. 29) and the measurement time (throughput) also improved by a factor of 5.

L-PAS sensors have applications in the industrial (petrochemical, semi-conductor industries), security (chemical warfare agent and explosives detection), and medical (breath analysis) fields. The smart grid algorithm for L-PAS improves PFA and measurement time for all L-PAS sensors, regardless of their application or target species.

The use of the Smart Grid algorithm is suitable for all other sensors based on spectral data and where interferences are present.

Performance Optimization

An iterative laser tuning algorithm is achievable for detection of a target species which tunes the laser to the more distinct (interference free) and large absorption frequency ranges in the absorption spectrum of the target species first to achieve fast detection with a high probability and then adaptively move on to wider frequency ranges when lower False Alarm Rates (FAR) are required (FAR is frequently referred to as PFA). This algorithm optimizes laser photoacoustic spectroscopy (L-PAS) throughput vs. performance in the presence of interferents that cannot be rejected. The performance optimization algorithm permits a quantification of the L-PAS instrument performance as a function of throughput and an optimization of the L-PAS instrument performance for a given throughput requirement.

Gas detection using photoacoustic spectroscopy involves tuning a laser across different frequencies and recording the acoustic signal from the cell. When this signal is recorded across different frequencies it produces a unique signature for each molecule. In the real world, gas samples are composed of many different molecules (a "soup"). When the signature of the soup is linearly deconvolved against a standardized library of the target species, and a list of expected interferents, it produces a concentration reading for the target gas.

L-PAS is very useful for sub-ppb (parts per billion) detection of gas species. However tuning the laser across many different frequencies and collecting photoacoustic data can be a time consuming process. L-PAS sensors have a wide variety of applications, in the industrial (petrochemical, semiconductor industries), security (chemical warfare agent and explosives detection), and medical (breath analysis) fields. Many of these applications require rapid response times, and immediate action to be taken when threats are detected. Hence there is a great need to speed up measurements sometimes even at the expense of higher false alarm rates.

The iterative laser tuning algorithm for detection of a target species tunes the laser to the more distinct (interference free) and large absorption frequency ranges in the absorption spectrum of the target species first.

Quick scans are performed in this range to obtain gas measurements with a high probability of detection (PD) and relatively high false alarm rate (FAR). Once the target species is detected above a certain threshold, the laser is tuned across a broader frequency range to obtain more interference free measurements with high PD and lower FAR.

To achieve optimized performance, the following procedure may be used with the following inputs and steps.

Inputs:
1) Alarm Threshold; and
2) Minimum Throughput Rate

Steps:
1) Identify and select a region in the frequency range of the laser which meets all the following criteria:
   a) Target species has large absorption
   b) Expected interferents have low absorption at their expected concentrations; and
   c) Signature of target is linearly independent of signature of interferents.
2) Perform a scan across the region and collect photoacoustic data.
3) Linearly deconvolve photoacoustic data against a standard library of the target species and list of expected interferents, and obtain a gas concentration measurement.
4) Record measurement and determine time taken for the measurement (throughput).
5) If the gas concentration is below the alarm threshold continue to Step without making any changes.
6) If all the following conditions are met:
   a) Gas concentration is above the alarm threshold;
   b) Throughput rate above minimum throughput rate; and
Selected region is not already the maximum tunable range of the laser, and select a new broader range which meets all the criteria mentioned in Step 1 as well as not violating the requirement for minimum allowable throughput.
7) Continue to Step 2.

For demonstration purposes, we chose our target as TNT and ammonium nitrate to be our interferent. We chose a region in the TNT spectrum where a broad and strong absorption feature is seen, and where the absorption feature of ammonium nitrate is relatively small and linearly independent of the TNT feature. We provided a continuous flow of CDA over a sample of TNT and the emerging gas was continuously analyzed by our spectrometer. The gas transport lines from the TNT sample chamber to the PA cell were maintained at 78 C and the PA Cell was maintained at 60 C.

We identified 3 regions for analysis. The first range we called "L-PAS Range 1" 120 (FIG. 30) which consisted of 5 discrete frequency points near the peak of the TNT absorption feature to do our analysis. "L-PAS Range 2" 122 was selected to be a wider region around the TNT absorption peak consisting of 50 discrete frequency points. The third region was "Full L-PAS Range" 124 and represented the full usable tuning range of our laser for TNT detection consisting of 150 discrete frequencies.

Figure 30:
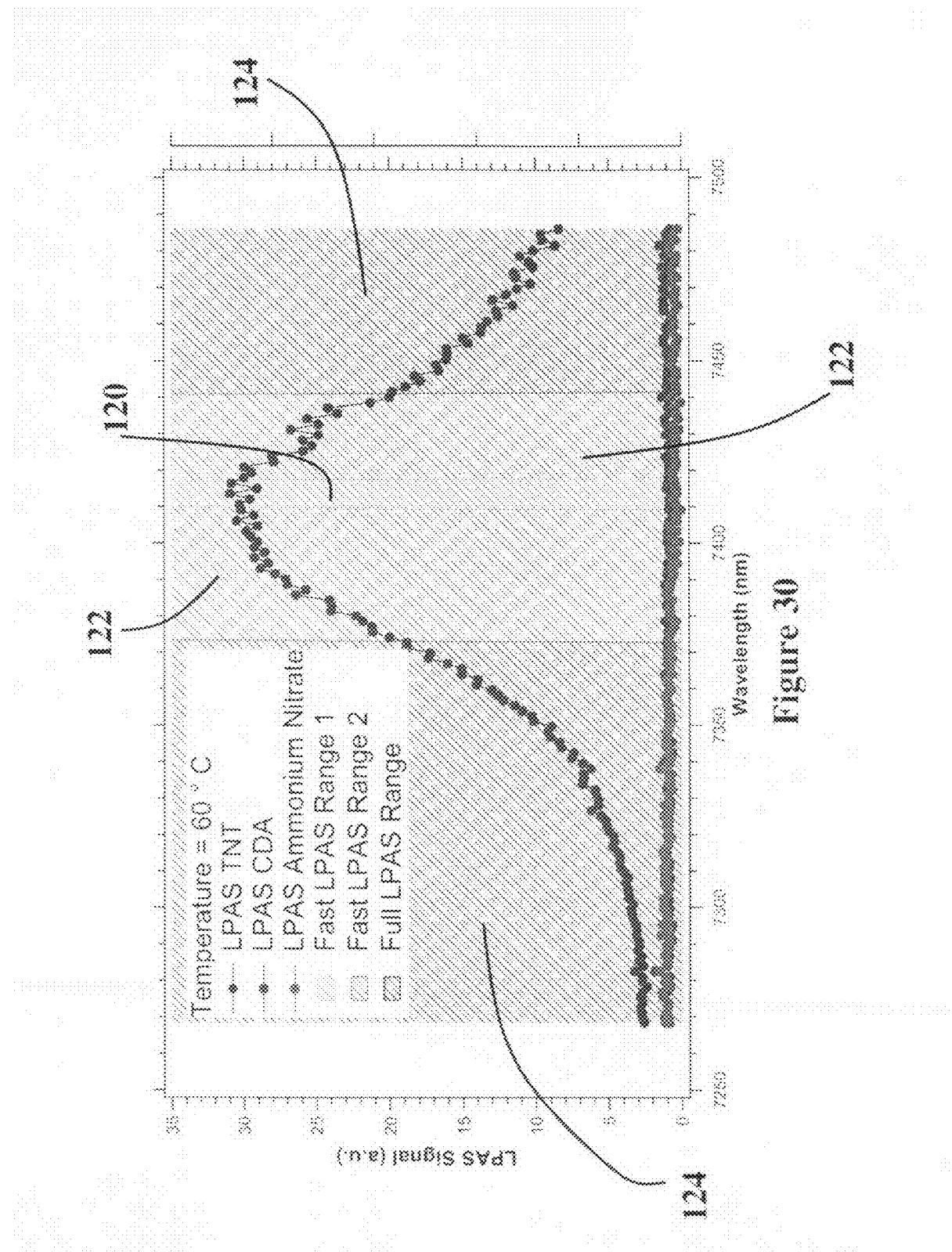
FIG. 30 is a diagram showing L-PAS absorption spectra of TNT indicating different ranges used for analysis.
Figure 31:
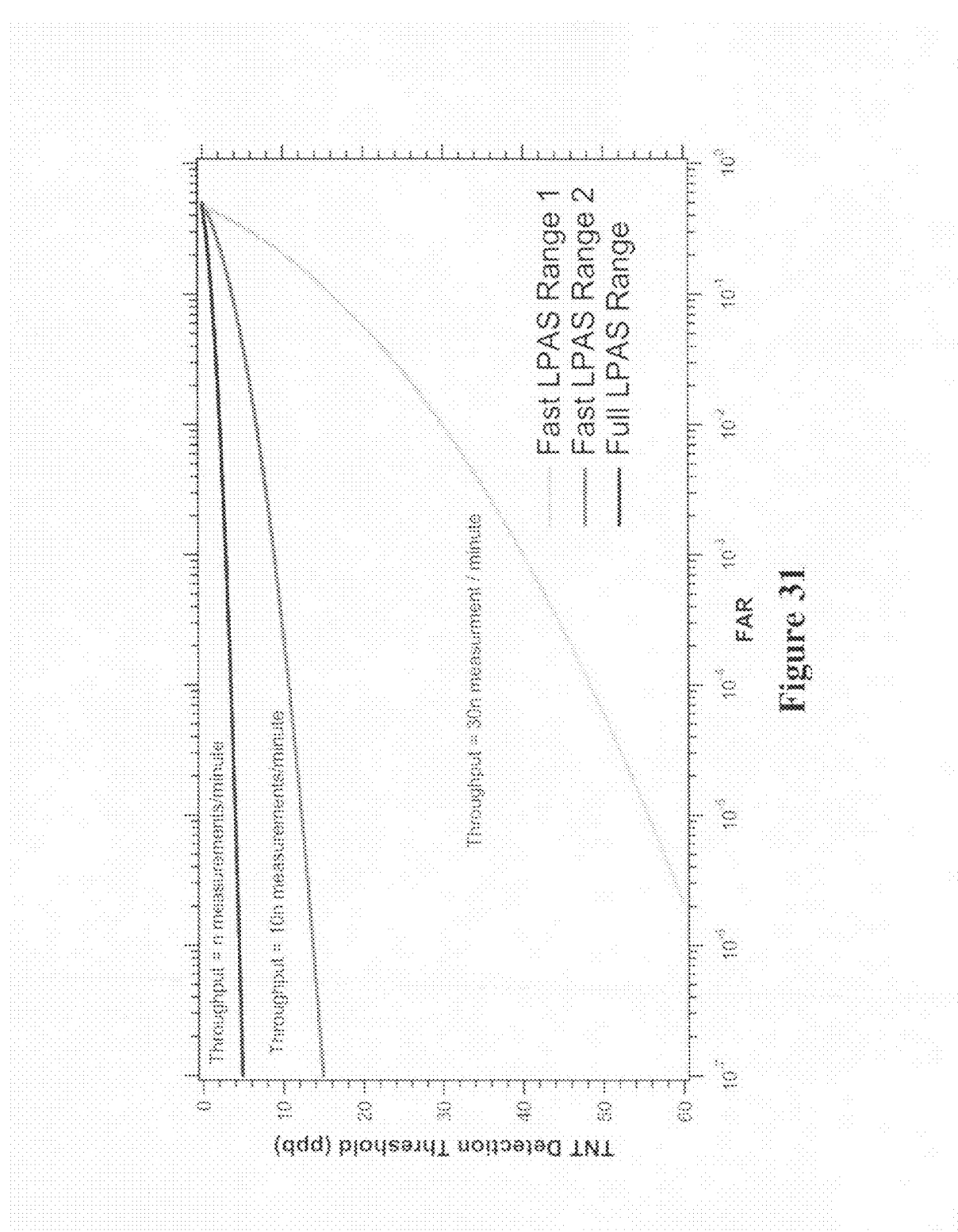
FIG. 31 is a diagram showing TNT Detection threshold vs. Probability of False Alarms for the different spectral ranges seen in FIG. 30.

FIG. 30 shows the TNT absorption spectrum as seen on our setup and the different ranges we used for analysis of the spectrum. FIG. 31 shows the Detection Threshold vs. the Probability of False Alarms for each one of these regions. The figure demonstrates the tradeoff between FAR and system throughput and quantitative data for the user.

L-PAS sensors have applications, in the industrial (petrochemical, semi-conductor industries), security (chemical warfare agent and explosives detection), and medical (breath analysis) fields. Quantifying instrument performance as a function of throughput and being able to optimize performance for a required throughput level can make sensors tunable to combat various scenarios, and can save time, money and lives in numerous situations. Here we look at 2 scenarios where this algorithm would prove helpful. This algorithm will prove suitable for all other optical sensors.

Scenario 1: Baggage Screening Checkpoint at an Airport

For a more efficient throughput rate at a baggage screening checkpoint as a first line of defense, explosive detection systems that detect a wide array of threats, with high throughput and a higher FAR can be used. The baggage items that fail the initial screening can be again tested with a second set of sensors with far lower FARs but with lower throughput.

Scenario 2: Cargo Screening Checkpoint at a Port

For a cargo screening system to detect Explosives and Chemical Warfare Agents, L-PAS sensors can be tuned for different threat levels issued by the Department of Homeland Security. For a high threat level the Minimum Throughput Rate can be lowered to achieve a lower FAR. When the threat levels are low the Minimum throughput rate can be made higher, at the expense of higher FAR.

These and other advantages, utilities, applications, and solutions provided by the present invention will be apparent from a review of the specification herein and accompanying drawings. The foregoing are some of but a few of the goals sought to be attained by the present invention and are set forth for the purposes of example only and not those of limitation.

While the present invention has been described with regards to particular embodiments, it is recognized that additional variations of the present invention may be devised without departing from the inventive concept.

What is claimed is:

1. A method for obtaining power-maximized continuous tuning for a coupled cavity laser system, the steps comprising:
   a) powering a quantum cascade laser (QCL) gain chip to provide a source of multiwavelength laser light at a first power level;
   b) selectively reflecting said multiwavelength laser light with a diffraction grating in a cavity back to said QCL, gain chip to select a first laser wavelength;
   c) adjusting a position of said diffraction grating with a piezoelectric translator (PZT) to adjust a distance of said cavity to obtain a maximum output distance for said first laser wavelength and said first power level, said maximum output distance maximizing output of the laser system at said first laser wavelength, said position of said diffraction grating, selectively altered on the order of a few wavelengths of said first laser frequency to find said maximum output distance;
   d) making a fine angular displacement step with said diffraction grating to select a new laser wavelength and repeating steps b and c in an ongoing fashion for each new laser wavelength to obtain sufficient data to determine Fabry-Perot (FP) mode comb peaks for said QCL gain chip at said first power level over a desired wavelength range;
   e) determining a maximizing power level for said first wavelength by determining a mode comb power level of the QCL gain chip that causes a mode comb wavelength spike of said QCL gain chip to coincide with said first laser wavelength, said maximizing power level achieved by determining a first power level change to shift one of said laser output peaks a first known fractional FP mode distance to determine $\Delta I_{FSR}$, selecting a wavelength at which the laser will operate, determining a second fractional FP mode distance said selected wavelength is from a first output peak, and powering said QCL gain chip by a current equal to $$I = I_0 - \Delta I_{FSR} \frac{v_0}{v} \mathrm{mod}\left(\frac{v - v_0}{\Delta v_{FSR}}, 1\right),$$

where $I_0$—starting/maximum current (mA), $v_0$—starting frequency (cm$^{-1}$), v—frequency (cm$^{-1}$) at the current I (mA), and $\Delta I_{FSR}$—current change (mA) necessary to shift a Fabry-Perot comb of said source by exactly one free spectral range ($\Delta V_{FSR}$ cm$^{-1}$) in the vicinity of $v_0$, and determining maximizing power levels for each of the other wavelengths in said wavelength range in a similar manner;

f) incrementing or decrementing a selected determined maximizing power level to match a second selected laser wavelength within said wavelength range and shifting said maximizing power level a free spectral range amount when needed to maintain said maximizing power level within preferred power limits of said source while simultaneously matching said first laser wavelength;

g) adjusting a position of said diffraction grating at said maximum output distance with said piezoelectric translator (PZT) to ensure that said selected maximum output distance for said selected wavelength is as much a maximum output distance as possible to enable maximum output of the laser system at said selected laser wavelength; whereby the coupled cavity laser system operates at a maximum for a selected wavelength within said wavelength range by selecting and ensuring said maximum output distance and said maximizing power level for said selected wavelength.

2. A method for obtaining power-maximized continuous tuning for a coupled cavity laser system, the steps comprising:

a) powering a source of multiwavelength laser light at a first power level, said source of multiwavelength laser light including a quantum cascade laser (QCL) gain chip;

selectively reflecting said multiwavelength laser light in a cavity back to said source to select a first laser wavelength;

c) adjusting a distance of said cavity to obtain a maximum output distance for said first laser wavelength and said first power level, said maximum output distance maximizing output of the laser system at said first laser wavelength;

d) repeating steps b and c for other laser wavelengths to obtain sufficient data to determine laser output peaks for said source at said first power level over a desired wavelength range; and e) determining a maximizing power level for each wavelength in said wavelength range; whereby the coupled cavity laser system operates at a maximum for a selected wavelength within said wavelength range by selecting said maximum output distance and said maximizing power level for said selected wavelength;

wherein said step of determining a maximizing power level further comprises:

(i) determining a first power level change to shift one of said laser output peaks a first known fractional Fabry-Perot (FP) mode distance to determine $\Delta I_{FSR}$;

(ii) selecting a wavelength at which the laser will operate;

(iii) determining a second fractional FP mode distance said selected wavelength is from a first output peak; and (iv) powering said QCL gain chip by a current equal to $$I = I_0 - \Delta I_{FSR} \frac{v_0}{v} \mathrm{mod}\left(\frac{v - v_0}{\Delta v_{FSR}}, 1\right),$$

where $I_0$—starting/maximum current (mA), $v_0$—starting frequency (cm$^{-1}$), v—frequency (cm$^{-1}$) at the current I(mA), and $\Delta I_{FSR}$—current change (mA) necessary to shift a Fabry-Perot comb of said source by exactly one free spectral range ($\Delta v_{FSR}$ cm$^{-1}$) in the vicinity of $v_0$.

* * * * *